US012796980B2

(12) United States Patent
Kettenmann et al.

(10) Patent No.: US 12,796,980 B2
(45) Date of Patent: Nov. 17, 2026

(54) METHOD FOR DETERMINING RELIABILITY OF AN ANALYTE SENSOR

(71) Applicant: Roche Diabetes Care, Inc., Indianapolis, IN (US)

(72) Inventors: Peter Kettenmann, Waghaeusel (DE); Christian Ringemann, Mannheim (DE)

(73) Assignee: Roche Diabetes Care, Inc., Indianapolis, IN (US)

(*) Notice: Subject to any disclaimer, the term of this patent is extended or adjusted under 35 U.S.C. 154(b) by 425 days.

(21) Appl. No.: 18/496,686

(22) Filed: Oct. 27, 2023

(65) Prior Publication Data

US 2024/0049999 A1 Feb. 15, 2024

Related U.S. Application Data

(63) Continuation of application No. PCT/EP2022/060968, filed on Apr. 26, 2022.

(30) Foreign Application Priority Data

Apr. 29, 2021 (EP) .................................... 21171239

(51) Int. Cl.
*A61B 5/1495* (2006.01)
*A61B 5/145* (2006.01)

(52) U.S. Cl.
CPC ........ *A61B 5/1495* (2013.01); *A61B 5/14546* (2013.01)

(58) Field of Classification Search
CPC .............. A61B 5/1495; A61B 5/14546; A61B 2560/0223; A61B 5/7246; A61B 5/1451; A61B 5/14532; A61B 2560/0252; A61B 5/14735; A61B 5/14865; A61B 5/7221; A61B 5/7264
See application file for complete search history.

(56) References Cited

U.S. PATENT DOCUMENTS

| | | | | |
|---|---|---|---|---|
| 9,681,807 | B2 * | 6/2017 | Miller | A61B 5/0002 |
| 2003/0153820 | A1 | 8/2003 | Berner et al. | |

(Continued)

FOREIGN PATENT DOCUMENTS

| | | | |
|---|---|---|---|
| EP | 1 913 374 | B1 | 1/2019 |
| EP | 20162098.6 | | 3/2020 |

(Continued)

OTHER PUBLICATIONS

International Search Report and Written Opinion of the International Searching Authority, PCT/EP2022/060968, Jul. 7, 2022, 9 pages.

*Primary Examiner* — Daryl C Pope
(74) *Attorney, Agent, or Firm* — Bose McKinney & Evans LLP

(57) ABSTRACT

A method for determining the reliability of an analyte sensor is disclosed. The analyte sensor is an in vivo sensor. The method includes measuring at least one first temperature dependent signal, measuring at least one second temperature dependent signal which is different from the first temperature dependent signal and which is related to a current flow in the analyte sensor, and correlating the first temperature dependent signal and the second temperature dependent signal for determining the reliability of the analyte sensor.

19 Claims, 4 Drawing Sheets

(56) References Cited

U.S. PATENT DOCUMENTS

| | | | | |
|---|---|---|---|---|
| 2009/0066347 | A1* | 3/2009 | Uenluebayir | G01N 27/12 324/686 |
| 2011/0231105 | A1* | 9/2011 | Wu | G01N 27/3274 702/19 |
| 2016/0081597 | A1 | 3/2016 | Bhavaraju et al. | |
| 2017/0181672 | A1 | 6/2017 | Nogueira et al. | |
| 2019/0223765 | A1 | 7/2019 | Harley-Trochimczyk et al. | |
| 2019/0239778 | A1 | 8/2019 | Srinivasan et al. | |
| 2022/0369929 | A1* | 11/2022 | Seo | A61B 5/746 |

FOREIGN PATENT DOCUMENTS

| | | | |
|---|---|---|---|
| EP | 2697650 | B1 | 9/2020 |
| KR | 10-2013-0067320 | | 6/2013 |
| WO | WO 2019/147582 | A1 | 8/2019 |
| WO | WO 2021/180619 | A1 | 9/2021 |

* cited by examiner

METHOD FOR DETERMINING RELIABILITY OF AN ANALYTE SENSOR

RELATED APPLICATIONS

This application is a continuation of International Application Serial No. PCT/EP2022/060968, filed Apr. 26, 2022, which claims priority to EP 21 171 239.3, filed Apr. 29, 2021, the entire disclosures of both of which are hereby incorporated herein by reference.

BACKGROUND

This disclosure teaches a method for determining reliability of an analyte sensor, a method for determining a concentration of at least one analyte in bodily fluid (also referred to herein as "body fluid") using at least one analyte sensor, and an analyte sensor. The analyte sensor may be or may comprise an electrochemical sensor configured for insertion into a bodily tissue of a user, specifically an insertable or implantable electrochemical sensor for monitoring of the at least one analyte in the bodily tissue and/or in a bodily fluid within the bodily tissue. The method and devices according to this disclosure may be used for detecting at least one analyte present in one or both of a bodily tissue or a bodily fluid, in particular the method and devices are applied in the field of detecting one or more analytes such as glucose, lactate, triglycerides, cholesterol or other analytes, e.g., metabolites, in bodily fluids such as blood or interstitial fluid or other bodily fluids, both in the field of professional diagnostics, in the field of hospital point of care, in the field of personal care and in the field of home monitoring. However, other fields of application are feasible.

In the field of medical technology and diagnostics, a large number of devices and methods for detecting at least one analyte in a bodily fluid are known. The methods and devices may be used for detecting at least one analyte present in one or both of a bodily tissue or a bodily fluid, in particular one or more metabolites, in particular one or more analytes such as glucose, lactate, triglycerides, cholesterol or other analytes in bodily fluids such as blood or interstitial fluid or other bodily fluids. Without restricting the scope of this disclosure, in the following, mainly reference is made to the determination of glucose by an electrochemical biosensor as an exemplary and preferred analyte.

In particular for in vivo analyte sensors, ensuring reliability is a challenge. Known methods and devices use complex software routines implemented in the analyte sensor or automatic insulin dosing controlling circuitry in order to detect a failure of the analyte sensor. However, there is still a risk that the used algorithms fail to detect gradual malfunctions resulting in an erroneous insulin dosing. Known automatic insulin dosing circuitry therefore have implemented additional safety measures in order to minimize risk of patient hazard. However, such additional safety measures further increase complexity.

U.S. Publication No. 2016/0081597 A1 describes systems and methods for changing a required level of user interaction during use of a monitoring device. The systems and methods generally relate to real time switching between a first or initial mode of user interaction and a second or new mode of user interaction.

U.S. Publication No. 2017/0181672 A1 describes electrochemical impedance spectroscopy (EIS) used in conjunction with continuous glucose monitoring (CGM) to enable identification of valid and reliable sensor data, as well as implementation of Smart Calibration algorithms.

WO 2019/147582 describes systems and methods for compensating for the effects of temperature on sensors, such as analyte sensors. An exemplary method may include determining a temperature-compensated glucose concentration level by receiving a temperature signal indicative of a temperature parameter of an external component, receiving a glucose signal indicative of an in vivo glucose concentration level, and determining a compensated glucose concentration level based on the glucose signal, the temperature signal, and a delay parameter.

European Patent Application No. 20 162 098.6, filed on Mar. 10, 2020, describes a method for determining at least one membrane property of an analyte sensor. The analyte sensor comprises at least two measurement electrodes. At least one of the measurement electrodes comprises at least one membrane element having the at least one membrane property. The method comprises the following steps: a) generating at least one fast-transient voltage signal and applying the fast-transient voltage signal to the measurement electrodes; b) measuring at least one response signal; c) determining the at least one membrane property by evaluating of the response signal.

SUMMARY

This disclosure provides a method for determining a reliability of an analyte sensor, a method for determining a concentration of at least one analyte in bodily fluid using at least one analyte sensor and an analyte sensor, which at least partially avoid the shortcomings of known devices and methods of this kind and which at least partially address the above-mentioned challenges. Specifically, a method for determining a reliability of an analyte sensor, and a single fault safe analyte sensor with reduced complexity are taught herein.

As used in the following, the terms "have," "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B," "A comprises B" and "A includes B" may both refer to a situation in which, besides B, no other element is present in A (i.e., a situation in which A solely and exclusively consists of B) and to a situation in which, besides B, one or more further elements are present in entity A, such as element C, elements C and D or even further elements.

Further, it shall be noted that the terms "at least one," "one or more" or similar expressions indicating that a feature or element may be present once or more than once typically will be used only once when introducing the respective feature or element. In the following, in most cases, when referring to the respective feature or element, the expressions "at least one" or "one or more" will not be repeated, non-withstanding the fact that the respective feature or element may be present once or more than once. It shall also be understood for purposes of this disclosure and appended claims that, regardless of whether the phrases "one or more" or "at least one" precede an element or feature appearing in this disclosure or claims, such element or feature shall not receive a singular interpretation unless it is made explicit herein. By way of non-limiting example, the terms "temperature dependent signal," "measurement electrode," and "membrane," to name just a few, should be interpreted wherever they appear in this disclosure and claims to mean "at least one" or "one or more" regardless of whether they are introduced with the expressions "at least one" or "one or more." All other terms used herein should be similarly interpreted unless it is made explicit that a singular interpretation is intended.

Further, as used in the following, the terms "preferably," "more preferably," "particularly," "more particularly," "specifically," "more specifically" or similar terms are used in conjunction with optional features, without restricting alternative possibilities. Thus, features introduced by these terms are optional features and are not intended to restrict the scope of the claims in any way. The invention may, as the skilled person will recognize, be performed by using alternative features. Similarly, features introduced by "in an embodiment of the invention" or similar expressions are intended to be optional features, without any restriction regarding alternative embodiments of the invention, without any restrictions regarding the scope of the invention and without any restriction regarding the possibility of combining the features introduced in such way with other optional or non-optional features of the invention.

In a first aspect, a method for determining a reliability of an analyte sensor is disclosed.

The term "reliability" as used herein is a broad term and is to be given its ordinary and customary meaning to a person of ordinary skill in the art and is not to be limited to a special or customized meaning. The term specifically may refer, without limitation, to an ability of the analyte sensor to function without failure and/or within a tolerable error range. The tolerable error range may be predefined. The term "reliability of an analyte sensor" furthermore also encompasses the reliability of any measurement which is carried out by the sensor, such as a calibration, an analyte measurement etc. In this context "reliability" refers to a measurement without failure and/or within a tolerable error range.

The term "analyte" as used herein is a broad term and is to be given its ordinary and customary meaning to a person of ordinary skill in the art and is not to be limited to a special or customized meaning. The term specifically may refer, without limitation, to an arbitrary element, component or compound which may be present in a bodily fluid and the concentration of which may be of interest for a user. Specifically, the analyte may be or may comprise an arbitrary chemical substance or chemical compound which may take part in the metabolism of the user, such as at least one metabolite. As an example, the at least one analyte may be selected from the group consisting of glucose, cholesterol, triglycerides, lactate. Additionally or alternatively, however, other types of analytes may be determined and/or any combination of analytes may be determined.

The term "sensor" as used herein is a broad term and is to be given its ordinary and customary meaning to a person of ordinary skill in the art and is not to be limited to a special or customized meaning. The term specifically may refer, without limitation, to an arbitrary element or device configured for detecting at least one condition or for measuring at least one measurement variable.

The term "analyte sensor" as used herein is a broad term and is to be given its ordinary and customary meaning to a person of ordinary skill in the art and is not to be limited to a special or customized meaning. The term specifically may refer, without limitation, to a sensor configured for detecting quantitatively or qualitative at least one analyte. The analyte sensor may be or may comprise at least one electrochemical sensor. The term "electrochemical sensor" specifically may refer to a sensor based on electrochemical measurement principles, such as by using one or more of an amperometric, coulometric or a potentiometric measurement principle. The electrochemical sensor may be configured for electrochemical detection of the analyte. Specifically, the electrochemical sensor may comprise at least one enzyme configured for performing at least one redox reaction in the presence of the analyte to be detected, wherein the redox reaction may be detected by electrical means. As used herein, the term "electrochemical detection" refers to a detection of an electrochemically detectable property of the analyte by electrochemical means, such as an electrochemical detection reaction. Thus, for example, the electrochemical detection reaction may be detected by comparing one or more electrode potentials, such as a potential of a working electrode with the potential of one or more further electrodes such as a counter electrode or a reference electrode. The detection may be analyte specific. The detection may be a qualitative and/or a quantitative detection. The detection may comprise determining an analyte concentration.

In an embodiment, the analyte sensor may be an optical sensor. The term optical sensor specifically may refer to a sensor based on optical measurement techniques, such as light. Other embodiments are feasible.

The analyte sensor is an in-vivo sensor. The term "in-vivo sensor" as used herein is a broad term and is to be given its ordinary and customary meaning to a person of ordinary skill in the art and is not to be limited to a special or customized meaning. The term specifically may refer, without limitation, to a sensor which is configured for being at least partially implanted into a bodily tissue of a user. The analyte sensor may be a subcutaneous analyte sensor. The analyte sensor may be configured for implantation into a bodily tissue of the user. More specifically the analyte sensor may be configured for continuous monitoring of the analyte. The analyte sensor may be fully implantable or partially implantable.

The term "user" as used herein is a broad term and is to be given its ordinary and customary meaning to a person of ordinary skill in the art and is not to be limited to a special or customized meaning. The term specifically may refer, without limitation, to a human being or an animal, independent from the fact that the human being or animal, respectively, may be in a healthy condition or may suffer from one or more diseases. As an example, the user may be a human being or an animal suffering from diabetes. However, additionally or alternatively, this disclosure may be applied to other types of users.

The analyte sensor may comprise at least two measurement electrodes. The term "measurement electrode" as used herein is a broad term and is to be given its ordinary and customary meaning to a person of ordinary skill in the art and is not to be limited to a special or customized meaning. The term specifically may refer, without limitation, to an electrode which is or can be brought in contact with an electrolyte, in particular with a bodily fluid. The at least two measurement electrodes may be designed such that an electrochemical reaction may take place at one or more of the measurement electrodes. The measurement electrodes may be embodied such that an oxidation reaction and/or reduction reaction may take place at one or more of the measurement electrodes.

One of the measurement electrodes may be designed as working electrode. The term "working electrode" as used herein is a broad term and is to be given its ordinary and customary meaning to a person of ordinary skill in the art and is not to be limited to a special or customized meaning. The term specifically may refer, without limitation, to an electrode of the analyte sensor which is configured for measuring a signal, such as a voltage, a current, a charge or electrical/electrochemical potential, dependent on the degree of an electrochemical detection reaction taking place at the working electrode, for the purpose of detecting the at least one analyte. The working electrode may comprise at least one test chemical. The working electrode may fully or partially be covered with at least one test chemical, specifically at least one test chemical comprising at least one enzyme for detecting the at least one analyte. As an example, glucose oxidase (GOx) or glucose dehydrogenase (GDH) may be used. The test chemical, further, may comprise additional materials, such as binder materials, electrode particles, mediators or the like. Thus, as an example, the test chemical may comprise at least one enzyme, carbon particles, a polymer binder and $MnO_2$ particles. In another preferred embodiment, the test chemical may comprise a mediator polymer comprising a polymeric material and a metal containing complex, for example, a modified poly (vinylpyridine) backbone loaded with poly(bi-imidizyl) Os complexes covalently coupled through a bidentate linkage. Further, the at least one test chemical may be comprised in a single layer, or the test chemical may comprise a plurality of layers, such as one layer having the at least one enzyme and one or more additional layers having one or more additional functions, such as one or more diffusion barriers and/or one or more biocompatibility layers.

The other one of the measurement electrodes may be designed as counter or auxiliary electrode. The term "counter electrode" as used herein is a broad term and is to be given its ordinary and customary meaning to a person of ordinary skill in the art and is not to be limited to a special or customized meaning. The term specifically may refer, without limitation, to an electrode adapted for performing at least one electrochemical counter reaction and/or configured for balancing a current flow due to the detection reaction at the working electrode. The counter electrode may be a part of the implanted or partially implanted analyte sensor, or may be an individual electrode, which is either implanted or partially implanted or placed somewhere else on the body, e.g., on the skin surface. In case of the analyte sensor comprises a two-electrode system as measurement electrodes, the counter electrode may complete the circuit such that charge can flow through an electrochemical cell, also denoted electrochemical system, given by the working electrode, the counter electrode and an electrolyte, such as the bodily fluid, and may maintain a constant counter electrode potential, also referred to as a constant reference potential, regardless of current.

Additionally, the analyte sensor may comprise at least one reference electrode. The term "reference electrode," also referred to as "pseudo reference electrode," specifically may refer, without limitation, to an electrode of the analyte sensor which is configured to provide an electrochemical reference potential which, at least widely, is independent of the presence or absence or concentration of the analyte. The reference electrode may be configured for being a reference for measuring and/or controlling a potential of the working electrode. The reference electrode may have a stable and well-known electrode potential. The electrode potential of the reference electrode may preferably be highly stable.

One of the measurement electrodes may have several functionalities, as for instance, combined reference and counter electrode, which has both the function of the reference and counter electrodes, which means it provides a reference potential and balances the current flow from the working electrode.

The analyte sensor may comprise at least one membrane element, also referred to as a "membrane." Preferably, at least one of the measurement electrodes may comprise the at least one membrane element. Specifically, the membrane element may be applied to the working electrode. The term "membrane element" or "membrane" as used herein is a broad term and is to be given its ordinary and customary meaning to a person of ordinary skill in the art and is not to be limited to a special or customized meaning. The term specifically may refer, without limitation, to at least one element configured for controlling and/or limiting diffusion of the analyte to the electrode to which the membrane element is applied. Thus, the membrane element may be configured as diffusion limiting membrane. However, the membrane element may have even more functionalities, such as providing biocompatibility. The membrane element may have further functions such as blocking of leakage of components below the membrane element such as of the enzyme or other components comprised in any one of the at least two measurement electrodes. The membrane element may also be configured as a blocking membrane. As used herein, the term "blocking" may refer to preventing leakage of inner components of a sensitive layer of the working electrode but not to the analyte. The membrane element may be configured for maintaining of sensor integrity, by for instance keeping the enzyme or redox mediator from leaching, thus degradation of the whole sensor. Independently on the role of the membrane element, its altering may be compensated.

The membrane element may comprise at least one polymer. The membrane element may be applied to the working electrode as thin polymer film. For example, the membrane element may be or may comprise Poly-(4-(N-(3-sulfonatopropyl) pyridinium)-co-(4vinyl-pyridine)-co-styrene (5%/90%/5%) or hydrophilic Polyurethane (HP60D20), for example, available from Lubrizol®. For example, the membrane element may comprise at least one of the following polymer classes and/or their copolymer: Poly(4 vinyl pyridine), Polymethacrylate, Polyacrylate, Polyvinyl pyrrolidone, Polyvinyl alcohol (PVA), Polyethylene glycol.

The membrane element may have at least one membrane property. The term "membrane property" as used herein is a broad term and is to be given its ordinary and customary meaning to a person of ordinary skill in the art and is not to be limited to a special or customized meaning. The term specifically may refer, without limitation, to an arbitrary physical property of the membrane element influencing the determining of the analyte. Specifically, the membrane property may be permeability of the membrane element. The term "permeability" as used herein is a broad term and is to be given its ordinary and customary meaning to a person of ordinary skill in the art and is not to be limited to a special or customized meaning. The term specifically may refer, without limitation, to a material parameter characterizing transmission properties of the membrane element, specifically passing of substances through the membrane element. Further specifically, permeability may refer to permeability for a specific analyte since molecules and ions of the analytes may have different sizes, shapes and charge. Permeability of the membrane element can be determined via determining an electrical resistance of the membrane element. Permeability of the membrane element may be proportional to the membranes electrical resistance. Without being bound by theory, conductivity of bodily fluid is directly linked to so-called total dissolved solids whereby ions, such as H+, OH−, Na+, K+, Cl− and other have the most contribution. Therefore, also conductivity of the membrane element which has taken up the bodily fluid is directly linked to said total dissolved solids. The more charge carriers are present and the more mobile they are, the lower is a measured electrical resistance of the membrane element, by otherwise constant conditions, such as, e.g., cell geometry. Thus, the electrical resistance, or reversely, electric conductivity of the membrane element may depend on quantity and mobility of ions present in the membrane element.

In an embodiment, the permeability refers to the permeability of the membrane for glucose. The permeability of the membrane element for a specific analyte, in particular glucose, can be determined by evaluating the electrical resistance of the membrane element. The permeability of the membrane element for a specific analyte $p_{Analyt}$ may be determined by $p_{Analyt}$=f*p, wherein p is the permeability determined via the electrical resistance of the membrane element and f is a conversion factor. The conversion factor may be determined in calibration experiments using known glucose values.

The inventive method comprises the method steps as given in the corresponding independent claim and as listed as follows. The method steps may be performed in the given order. One or more of the method steps may be performed in parallel and/or in a time overlapping fashion. Further, one or more of the method steps may be performed repeatedly. Further, additional method steps may be present which are not listed.

The method comprising the steps:

a) measuring at least one first temperature dependent signal;

b) measuring at least one second temperature dependent signal which is different from the first temperature dependent signal and which is related to a current flow in the analyte sensor;

c) correlating the first temperature dependent signal and the second temperature dependent signal for determining the reliability of the analyte sensor.

Depending on the determined analyte concentration, erroneous measurement values determined by using the analyte sensor may imply a risk for the user and may result in wrong therapy decisions. The method may comprise mutually monitoring of the first temperature dependent signal and of the second temperature dependent signal by using the correlation of step c) such that the analyte sensor is single fault safe. Generally, determining of the analyte concentration may be temperature sensitive. For example, known batches of analyte sensors often have a temperature sensitivity of 7%/K. Thus, if the temperature decreases at the analyte sensor, the analyte sensor may show smaller values of analyte concentration. In case of failure, the electrochemical analyte sensor may be defect or at least one temperature sensor of the analyte sensor may be defect. It was found that said first temperature dependent signal and the second temperature dependent signal correlate with each other such that correct functioning of the analyte sensor and of the temperature sensor of the analyte sensor can be monitored by mutually monitoring of the first temperature dependent signal and of the second temperature dependent signal by using the correlation. Single fault conditions such as failure of the analyte sensor can, thus, be identified and appropriate means can be adopted to eliminate or reduce as far as possible consequent risks or impairment of performance. For example, a measurement value may be rejected.

The term "single fault safe," also denoted as intrinsically safe, as used herein is a broad term and is to be given its ordinary and customary meaning to a person of ordinary skill in the art and is not to be limited to a special or customized meaning. The term specifically may refer, without limitation, to a property of the analyte sensor to ensure repeatability, reliability and performance in line with its intended use. Specifically, the analyte sensor may ensure that in the event of a single fault condition, appropriate means shall be adopted to eliminate or reduce as far as possible consequent risks or impairment of performance.

The terms "first" and "second" as used herein are broad terms and are to be given their ordinary and customary meaning to a person of ordinary skill in the art and are not to be limited to a special or customized meaning. The terms specifically may indicate a name, without limitation such as with respect to temporal order.

The term "first temperature dependent signal" as used herein is a broad term and is to be given its ordinary and customary meaning to a person of ordinary skill in the art and is not to be limited to a special or customized meaning. The term specifically may refer, without limitation, to an arbitrary signal being a measure for a first temperature and/or a first temperature gradient. The first temperature dependent signal may be a signal relating directly to the first temperature or a signal from which the first temperature is derivable. The first temperature dependent signal may be or may comprise at least one electrical signal, such as at least one analogue electrical signal and/or at least one digital electrical signal. More specifically, the first temperature dependent signal may be or may comprise at least one voltage signal and/or at least one current signal. Either a raw signal may be used or a processed or a preprocessed signal, such as preprocessed by filtering or the like.

The first temperature dependent signal may be measured by using at least one temperature sensor. The first temperature dependent signal may be measured by using a plurality of temperature sensors such as two, three or more temperature sensors. The first temperature dependent signal may be a temperature value which is measured by the temperature sensor and/or which is determined from a signal measured by the temperature sensor. The temperature sensor may be at least one sensor selected from the group consisting of: at least one thermistor such as at least one NTC-thermistor, PTC-thermistor, at least one thermocouple, and the like. The first temperature dependent signal may be measured in an on body part of the analyte sensor. The first temperature dependent signal may be measured by at least one temperature sensor comprised by an on body part of the analyte sensor. The analyte sensor may comprise an implantable part and an on body part. The term "implantable part" may refer to the elements of the analyte sensor performing a detection reaction for determining the concentration of the at least one analyte. The term "on body part" may refer to sensor electronics of the analyte sensor configured for performing the measurements. The on body part may comprise at least one circuit board. The on body part may comprise at least one microcontroller unit, wherein the microcontroller unit may be arranged on the circuit board. For example, the temperature sensor may be arranged in the microcontroller unit. For example, additionally or alternatively, the temperature sensor may be arranged in a housing of the analyte sensor close to the skin.

The term "second temperature dependent signal" as used herein is a broad term and is to be given its ordinary and customary meaning to a person of ordinary skill in the art and is not to be limited to a special or customized meaning. The term specifically may refer, without limitation, to an arbitrary signal related to a current flow in the analyte sensor being a measure for a second temperature and/or a second temperature gradient. The term "second temperature dependent signal related to current flow in the analyte sensor" as used herein is a broad term and is to be given its ordinary and customary meaning to a person of ordinary skill in the art and is not to be limited to a special or customized meaning. The term specifically may refer, without limitation, to measurable temperature behavior of ion mobility within a membrane element. The membrane element may comprise two properties a temperature dependent diffusion property for the analyte to be determined (i.e., permeability) and a temperature dependent electrical resistance. The membrane property, in particular the permeability, may depend on temperature. The second temperature dependent signal may be or may be related to an electrical resistance of the membrane element. Permeability of the membrane element may depend on temperature, as it directly influences the ions mobility within the membrane element. The temperature at an insertion site of the analyte sensor may not be constant. Intrinsic properties of the membrane element may change during storage of the analyte sensor such as due to storage conditions. Such changes may lead to changes in permeability and may lead to non-reliable measurements.

The first temperature dependent signal and the second temperature dependent signal may be independent signals, in particular determined using different measurement techniques and/or sensors. For example, the first temperature dependent signal may be measured using at least one temperature sensor, whereas the second temperature dependent signal may be measured using the so called "fast-transient-technique" which is described in the following. The "fast-transient-technique" is further described, e.g., in European Patent Application No. 20 162 098.6 filed on Mar. 10, 2020, the full content of which is included by reference.

Measuring the second temperature dependent signal in step b) may comprise applying at least one fast-transient voltage signal to the measurement electrodes and measuring a response signal, in particular the second temperature dependent signal, in response to the applied fast-transient voltage signal.

The term "fast-transient voltage signal," also denoted as fast-transient voltage, as used herein is a broad term and is to be given its ordinary and customary meaning to a person of ordinary skill in the art and is not to be limited to a special or customized meaning. The term specifically may refer, without limitation, to at least one arbitrary voltage change in between two measurement electrodes. The arbitrary voltage change may have fast transient signal flanks, in particular two very steep edges. The fast-transient voltage signal may comprise a square wave signal form and/or a sine wave signal form.

The fast-transient voltage signal may comprise a non-continuous signal such as a pulse. Specifically, the fast-transient voltage signal may comprise a fast transition square wave. The term "pulse" as used herein is a broad term and is to be given its ordinary and customary meaning to a person of ordinary skill in the art and is not to be limited to a special or customized meaning. The term specifically may refer, without limitation, to a signal having a transient change in the amplitude of the signal from a first value, also denoted baseline value, to a second value, followed by a return to the baseline value or at least approximately to the baseline value. The second value may be a higher or lower value than the baseline value. A pulse duration may be ≤50 μs, preferably ≤20 μs, more preferably ≤10 μs. The duration of the single pulse must be sufficiently long to be able to record its propagation. The duration of the single pulse must be preferentially short, in order to not excite the system electrochemically.

The fast-transient voltage signal may be applied during at least one test sequence, for example, a time sequence. The fast-transient voltage signal may be applied repeatedly, in particular periodically. The time distance between the cycles must be sufficiently long in order to keep the system at its steady-state. The fast-transient voltage signal may comprise a repeatable cycle, wherein the repeatable cycle comprises at least one signal flank. The pulse may comprise two edges: the leading edge or front edge, which is the first edge of the pulse and the trailing edge or back edge, which is the second edge of the pulse. The terms first and second "value" may refer to regions or points of the fast-transient voltage signal, in particular its amplitude. The first value may be the baseline value. The first value may be a local and/or overall minimum of the fast-transient voltage signal. The first value may be a first plateau of the fast-transient voltage signal. The first value may refer to a time point with no voltage is applied to the measurement electrodes. The first value may be the DC polarization voltage of the sensor. The second value may be a local and/or overall extremum of the fast-transient voltage signal. The second value may be a second plateau of the fast-transient voltage signal, which may be reached during application of the fast-transient voltage. The second value may be extremum of the fast-transient voltage signal.

The term "signal flank" as used herein is a broad term and is to be given its ordinary and customary meaning to a person of ordinary skill in the art and is not to be limited to a special or customized meaning. The term specifically may refer, without limitation, to transition of a signal amplitude from low to high signal value or from high to low signal value. The signal flank may be a rising signal flank or a falling signal flank. The signal flank of the fast-transient voltage signal may have a change in signal from the first value of the signal flank to the second value of the signal flank in a microsecond to nanosecond range. The signal flank of the fast-transient voltage signal may have a change in signal from the second value of the signal flank to the first value of the signal flank in a microsecond to nanosecond range. The signal flank may also be referred to as edge.

The fast-transient voltage signal may have a low-to-high transition of a signal amplitude, which is equivalent to rising or positive signal flank, or high-to-low transition of a signal amplitude, which is equivalent to falling or negative signal flank. The fast-transient voltage signal may have steep edges. The signal flank, in particular edge, of the fast-transient voltage signal may have a change from the first value to the second value in a microsecond to nanosecond range. The signal flank of the fast-transient voltage signal may have a change from the second value to the first value in a microsecond to nanosecond range. Specifically, the fast transition square wave may have a change in voltage from the first value to the second value below 50 ns, preferably below 20 ns. The change in voltage from the first value to the second value may be even faster and may be only limited by electronics such as by a fast-transient voltage generator, e.g., comprising at least one digital to analog converter (DAC) and/or at least one digital output (DO) or the like, or the measurement unit, e.g., comprising at least one voltage amplifier, ADC, or the like. The faster the change of voltage (higher slew rate) and the sharper a transition to a plateau, the more precise the membrane property can be determined.

The term "fast-transient" as used herein is a broad term and is to be given its ordinary and customary meaning to a person of ordinary skill in the art and is not to be limited to a special or customized meaning. The term specifically may refer, without limitation, to a time range between first and second values of the signal flank. The fast-transient voltage signal may have a rising signal flank and a falling signal flank. The fast-transient voltage signal may have steep edges. Specifically, the fast transition square wave may have a change in signal from the first value of the signal flank to the second value of the signal flank below 50 ns, preferably below 20 ns. The change in signal from the first value of the signal flank to the second value of the signal flank may be even faster and may be only limited by electronics such as by an analog-to-digital-converter. The faster the flank and the sharper the transition to the plateau, the more resolution may be between the ohmic part of the system resistance and the capacitive part of the system capacitance.

The duration of the single fast-transient voltage signal must be sufficiently long to record the response voltage. The duration of the single fast-transient voltage signal must be sufficiently short, in order to avoid system perturbation.

Without wishing to being bound by theory, the fast-transient voltage signal, in particular the voltage pulse, is so short, in particular ultrashort, that no faradaic currents are generated and that an electrochemical system of the analyte sensor is not disturbed and brought out of equilibrium. The ultrashort voltage of the fast-transient voltage signal for determining the membrane property may allow that a measurement signal for determining the analyte concentration can be undisturbed determined. The ultrashort voltage signal may prevent that side reaction occur. Moreover, the method according to this disclosure may allow to stay in the so-called time domain such that there is no need to transform to the so-called frequency domain.

An amplitude of the fast-transient voltage may vary in a broad range and must be optimized for a given set-up. Generally, the lower limit may be limited by the readout technique, which must record the response voltage, mostly by its input range and resolution and may require an additional sufficiently fast voltage amplifier.

The fast-transient voltage signal may comprise a repeatable cycle, wherein the repeatable cycle comprises at least one signal edge. The fast-transient voltage signal may be applied during at least one test sequence, for example, a time sequence. The fast-transient voltage signal may be applied repeatedly, in particular periodically. The interval between the cycles may be sufficiently long in order to let the double layer capacitance and the shunt capacitor to recharge to their previous steady-state voltage. The discharge of these capacitances after stop of the fast-transient voltage signal applying, as described above, means current flow opposite to the analyte current and thus distortion of the signal. Thus, the data acquisition for the recharging time may be stopped or the corresponding acquired samples may be ignored.

The fast-transient voltage signal may be applied repeatedly to the measurement electrodes, in particular in time intervals from minutes to seconds. For example, the fast-transient voltage signal may be applied repeatedly in 5 minutes-intervals.

The fast-transient voltage signal may be generated by at least one signal generator device. The term "signal generator device" generally refers to a device, for example, a voltage source, being configured to generate a voltage signal. The "signal generator device" may also be referred to as "voltage generating device." The signal generator device may comprise at least one voltage source. The signal generator device may comprise at least one function generator selected from the group consisting of: at least one square wave generator and at least one sine wave generator. The signal generator device may also generate a single pulse which may be unsymmetrical. "Unsymmetrical" in this context means that a first pulse may be different from a second pulse and/or a third pulse and/or any other subsequent pulse. The signal generator device may be part of sensor electronics of the analyte sensor and/or may be connected to the analyte sensor and may be designed as a separate device. The signal generator device may be configured for applying the fast-transient voltage signal to the measurement electrodes. The fast-transient voltage signal may be applied to at least two measurement electrodes in at least one signal application step.

The term "applying the fast-transient voltage signal to the measurement electrodes" as used herein is a broad term and is to be given its ordinary and customary meaning to a person of ordinary skill in the art and is not to be limited to a special or customized meaning. The term specifically may refer, without limitation, to applying the fast-transient voltage signal to one of the measurement electrodes, in particular to the working electrode.

The term "response signal" as used herein is a broad term and is to be given its ordinary and customary meaning to a person of ordinary skill in the art and is not to be limited to a special or customized meaning. The term specifically may refer, without limitation, to measured propagation of the applied fast-transient voltage signal. The terms "response signal" and "propagation" are used herein as synonyms. The response signal may be a change of the applied fast-transient voltage signal. The response signal may directly or indirectly refer to equivalent series resistance of the analyte sensor. The response signal may be the ohmic and capacitive characterization of the analyte sensor in its in-vivo surroundings. In particular, the response signal does not relate to current response. The response voltage may be determined either at a known reference resistor or at the membrane element.

The measuring of the response signal, in particular of the second temperature dependent signal, may be performed using the at least one measurement unit. The term "measurement unit" as used herein is a broad term and is to be given its ordinary and customary meaning to a person of ordinary skill in the art and is not to be limited to a special or customized meaning. The term specifically may refer, without limitation, to an arbitrary device, preferably at least one electronic device, which may be configured to detect at least one signal, in particular the response signal. The measurement unit may be configured for measuring the response signal generated in response to fast-transient voltage signal. As will be outlined in more detail below, the measurement unit may further be configured for measuring the current at the counter electrode for determining a concentration of at least one analyte in bodily fluid. The measurement unit may be configured for receiving the response signal and the current at the counter electrode at the same time or at least two different time points. The measurement unit may in particular be part of the on body part of the analyte sensor.

The measurement unit may comprise at least one potentiostat such as at least one digital potentiostat or at least one analog potentiostat. The analyte sensor may comprise and/or may be connected to the measurement unit, in particular to the at least one potentiostat or galvanostat. The measurement unit may be configured for determining the concentration of the analyte. Operating principles of potentiostats and galvanostats are generally known to the person skilled in the art. In the following the measurement unit will be described with reference to a potentiostat.

The potentiostat may be configured for monitoring and maintaining the potential between the reference electrode and the working electrode. The potentiostat may be configured for monitoring and maintaining the potential between the combined counter-reference electrode and the working electrode. The potentiostat may be configured for maintaining the desired polarization voltage, for example, 50 mV, between the reference electrode and the working electrode or between the working electrode and the combined counter-reference electrode. The current flowing between the working and the counter or the combined counter-reference electrode may be measured at the working or the counter or the combined counter-reference electrode. The reference electrode may be used to monitor the potential of the working electrode.

In order to perform the determining of the membrane property with high accuracy, acquisition of the response signal, in principle, must happen immediately after the fast-transient voltage signal is applied, because of a profile of the fast-transient voltage signal. Once the fast-transient voltage signal is applied at the analyte sensor, the analyte sensors' capacitive parts, such as double layer capacitance, are starting to charge. At the very beginning, the capacitive parts can be considered as a short cut, and, thus, corresponding resistive parts are short cut and do not play any role in the voltage drop across the analyte sensor. As longer the potential pulse continues, as more the capacitive parts in the analyte sensor may get charged, which may result in an additional voltage drop over these capacitors and, thus, also over the resistive parts so that the measurement may get inaccurate. In order to avoid undesired voltage distribution, as described above, the applied fast transient voltage signal must be as short as possible. Theoretically, the fast-transient voltage signal may be infinitely short. In practice, modern electronics may be sufficiently fast to reach a desired voltage magnitude within few ns. Usually, a limiting factor may be an acquisition speed of measurement electronics of a measurement unit such as of an analog-to-digital-converter (ADC), which is limited. The measurement electronics such as the ADC may convert an input voltage in digital form and compare it internally with internally generated and digitalized voltages (Successive-Approximation ADC). This process is called conversion. A minimal duration of this process may be determined by resolution and clock of the ADC, and takes, typically, few µs or less. Prior to this conversion, the input voltage may be sampled within an ADC channel. This is typically done by charging a small internal capacitor. Therefor the ADC may have corresponding switches: during the sampling, an external voltage to be determined is connected to the internal capacitor of the ADC. Once the capacitor is fully charged, it has the same voltage at its terminals as the input voltage to be determined. After that, the switches disconnect the external voltage and connect the capacitor to the internal converting and comparing unit. A limiting factor during this sampling phase may be the time, which is needed to charge the internal capacitor. Sampling time can be configured programmatically, but may not be lower, as needed for the full capacitor charge, otherwise the voltage at the internal capacitor does not reach the input value and the measurement is then wrong. Thus, the acquisition of the voltage value at the measurement electronics' input may take few microseconds because of the sampling and the conversion.

In particular, the method may comprise generating at least one fast-transient voltage signal and applying the fast-transient voltage signal to the measurement electrodes, measuring a response signal and determining the membrane property by evaluating of the response signal. The determining of the membrane property according to this disclosure may comprise determining the membrane property using a fast-transient technique as described in European Patent Application No. 20 162 098.6, filed on Mar. 10, 2020, the full content of which is included by reference. The evaluating of the response signal may comprise determining equivalent series resistance of the analyte sensor and determining the at least one membrane property from the unknown equivalent series resistance of the analyte sensor. The unknown equivalent series resistance to be determined may be serially connected with a known reference resistor. The reference resistor may have a value roughly matching the range of the unknown resistance, as will be described in more detail below. A signal generator device may apply a short voltage pulse at the two serially connected resistances. Simultaneously, voltage drop at one of the both resistors may be measured: either at the reference one, or at the unknown. Knowing the applied voltage and the voltage drop at one of the both resistances, may allow the value of the unknown resistance to be calculated. The described technique may demand minimum of additional components, which are needed to implement the fast-transient technique in an existing, in particular, digital potentiostat.

Specifically, determining of the membrane property, in particular a membrane resistance, may comprise generating the at least one fast-transient voltage signal $U_{gen,pulse}$ and applying it to a membrane comprising circuit serially connected with the reference resistor $R_{ref}$, wherein the membrane element has a resistance $R_{mem}$, recording a voltage $U_{meas,pulse}$ either at the reference resistor $R_{ref}$ or at the membrane element comprising circuit $R_{mem}$, determining the at least one membrane property by calculating the $R_{mem}$ from $U_{gen,pulse}$, $U_{meas,pulse}$ and $R_{ref}$. A simplified circuit may comprise the analyte sensor, represented as a simple Randle's circuit, the reference resistor $R_{ref}$, a measurement resistor $R_{meas}$, a shunt capacitor $C_{shunt}$, the signal generator device, in particular a voltage source, and a voltmeter (V). The Randle's circuit may comprise the charge transfer resistance $R_{ct}$, which represents the diffusion limited analyte current, double layer capacitance $C_{dl}$ at the electrode surface and the membrane element resistance $R_{mem}$. The signal generator device may be configured for applying a DC base voltage $U_{gen,base}$ and fast-transient voltage $U_{gen,pulse}$. During the DC base voltage is applied, the current flows through all four resistors in the circuit. There is no current flow through the capacitors, as they are charged to the corresponding level. The $R_{ct}$ may be a few orders of magnitude larger, than $R_{mem}$, such that the voltage drop at the $R_{mem}$ can be neglected in the first approximation. The same may be valid for the $R_{ref}$, which is chosen to be roughly the same value as the $R_{mem}$. The value for $R_{meas}$ may be chosen at the way, to get substantial voltage drop at it, which is then measured, e.g using an additional voltmeter or electrometer and converted in the response signal, also denoted sensor current signal. Thus, the value of the $R_{meas}$ may be roughly of the same order of magnitude as the $R_{ct}$. Since the voltage drop at the $R_{meas}$ is substantial, it may be compensated by the voltage source, which is in a feedback with the current measuring unit based on the $R_{meas}$. The calculation of the $R_{mem}$ may be done as $$R_{mem} = R_{ref}\frac{U_{meas,pulse}}{U_{gen,pulse} - U_{meas,pulse}}$$

The first temperature dependent signal and the second temperature dependent signal may be independent from at least one measurement signal of an analyte concentration measured by the analyte sensor. The potentiostat may be configured for generating and/or applying of at least one measurement voltage signal, in particular a polarizing potential or voltage, for measuring the measurement signal of an analyte concentration in response. As used herein, the term "measurement voltage signal" may refer to a voltage signal used for determining, in particular measuring, the concentration of the analyte. The measurement voltage signal may be different to the fast-transient voltage signal. In particular, the measurement voltage signal may be longer compared to the fast-transient voltage signal. The measurement voltage signal may be a permanent signal, not a pulsed one. The measurement voltage signal may be adjusted from time to time or continuously in order to give the analyte sensor its polarization voltage, preferably, in order to keep the predefined polarization voltage at the analyte sensor. The measurement voltage signal may be a continuous direct current (DC) signal which polarizes the electrochemical cell, and serves as the "motor" for the amperometric measurement of the analyte reducing or oxidizing GOx across the electrochemical cell. The fast-transient voltage signal may be a voltage pulse with high frequency that only characterizes the capacitive and ohmic parts of the electrochemical cell. Therefore, the measurement voltage signal and the fast-transient voltage signal may not influence each other, since they have completely different time domains.

In a two-electrode system, the measurement voltage signal and the fast-transient voltage signal may be applied to the same electrodes. In a three-electrode system a voltage is determined and controlled between the working electrode and the reference electrode. In order to achieve this, the potentiostat may regulate the potential of the counter electrode. The fast-transient voltage signal may be applied between the counter and the working electrode or between the working and the reference electrode or between the counter and the reference electrode.

As outlined above, the measuring of the response signal may be performed using the at least one reference resistor. Before the application of the fast-transient voltage signal the measurement unit, in particular the potentiostat, may measure the measurement voltage only. During the application of the fast-transient voltage signal, the potentiostat determines the sum of the measurement voltage signal and the fast-transient voltage signal. The potentiostat may be configured for determining the propagation of the fast-transient voltage signal applied to the working electrode. The potentiostat may be configured for determining a change or difference $\Delta V_{ex}$ of the voltage signal at the reference resistor before application of the fast-transient voltage signal and during the application of the fast-transient voltage signal. The potentiostat may be configured for determining a change or difference $\Delta V_{prop}$ of voltage at the working electrode before application of the fast-transient voltage signal and during the application of the fast-transient voltage signal.

The reference resistor may have a resistance, also denoted reference resistance, suitable for determining a value to be measured such as the electrical resistance of the membrane element. The reference resistance may be an average value determined, specifically predetermined, from a plurality of reference measurements. The reference resistance may reflect the measurement range of the membrane element. The reference resistance may reflect required measurement tolerances which have to be maintained for correct membrane element property, in particular membrane resistance.

An equivalent circuit of the electrochemical system of the analyte sensor, may comprise for each of the working electrode and the counter electrode a double layer capacitance in parallel with a charge transfer resistance, as outlined above. The resistance of the electrolyte between the working electrode and the reference electrode may be given by an electric resistance $R_2$ and the resistance of the electrolyte between the counter electrode and the reference electrode may be given by an electric resistance $R_1$. The resistance $R_2$ may further be dependent on properties of the membrane element.

For measuring the response signal, additional components may be used, in particular, in addition to the components of the potentiostat as described above. For example, the measurement unit may comprise additional capacitors and/or additional resistors. Specifically, the fast-transient voltage signal may be applied to one of the measurement electrodes, in particular the working electrode, in series with the reference resistance, denoted $R_3$ or $R_{ref}$. $R_{ref}$ may be a known reference resistance such as a predetermined reference resistance. As outlined above, the reference resistance may reflect the measurement range of the cell. The reference resistance may reflect required measurement tolerances which must be maintained for correct system resistances. The reference resistance may be selected suitable for determining a value to be measured such as the electrical resistance of the membrane element. The fast-transient voltage signal may be determined by using the reference resistor. Before the application of the fast-transient voltage signal the potentiostat determines the measurement voltage signal only. After the application of the fast-transient voltage signal the potentiostat determines the sum of the measurement voltage signal and the fast-transient voltage signal.

Measuring the second temperature dependent signal may comprise determining the at least one membrane property by evaluating of the response signal. In particular, the evaluating of the response signal comprises determining equivalent series resistance of the analyte sensor and determining the at least one membrane property from the equivalent series resistance of the analyte sensor. The evaluating of the response signal may comprise determining equivalent series resistance of the electrochemical system and determining the at least one membrane property from the equivalent series resistance of the electrochemical system. In order to measure the membrane property, in particular equivalent series resistance of the electrochemical system, the fast-transient voltage signal may be sent to the working electrode. The edges of the fast-transient voltage signal are very steep such that the additional capacitors and equivalent capacitors of the electrochemical system of the analyte sensor act like short-circuits. The equivalent series resistance of the electrochemical system may be determined by $$R_1 + R_2 = R_3\frac{\Delta V_{prop}}{\Delta V_{ex} - \Delta V_{prop}} = R_3\frac{V_{prop,duringPulse} - V_{prop,beforePulse}}{(V_{ex,duringPulse} - V_{ex,beforePulse}) - (V_{prop,duringPulse} - V_{prop,beforePulse})}$$

wherein $V_{prop,beforePulse}$ refers to the voltage at the working electrode before applying the fast-transient voltage signal, $V_{prop,duringPulse}$ refers to the voltage at the working electrode during applying the fast-transient voltage signal, $V_{ex,beforePulse}$ refers to the voltage signal at the reference resistor before applying the fast-transient voltage signal, $V_{ex,duringPulse}$ refers to the voltage signal at the reference resistor during applying the fast-transient voltage signal. Before the application of the fast-transient voltage signal $V_{ex,beforePulse}$ may refer to a voltage at the reference resistor in response to the measurement voltage signal. After the application of the fast-transient voltage signal $V_{ex,duringPulse}$ may refer to the voltage at the reference resistor in response to the measurement voltage signal and due to the propagation of the fast-transient voltage signal.

The term "correlating the first temperature dependent signal and the second temperature dependent signal" as used herein is a broad term and is to be given its ordinary and customary meaning to a person of ordinary skill in the art and is not to be limited to a special or customized meaning. The term specifically may refer, without limitation, to a process of determining a relationship between the first temperature dependent signal and the second temperature dependent signal. The correlating may comprise comparing a first temperature value determined from the first temperature dependent signal and a second temperature value determined from the second temperature dependent signal. The correlating may comprise determining a deviation between the first temperature value determined from the first temperature dependent signal and the second temperature value determined from the second temperature dependent signal. If the deviation $\Delta T = T_{first} - T_{second}$ between the first temperature value $T_{first}$ and the second temperature value $T_{second}$ is determined to exceed a threshold value $\Delta T_{threshold}$, the analyte sensor is considered as failed.

The correlating may comprise correlating at least one actual value of the first temperature dependent signal, in particular at least one first actual temperature value, and at least one actual value of the second temperature dependent signal, in particular at least one second actual temperature value. The respective actual value may be a mean value determined from a plurality of measurements such as during a measurement time range. For example, the measurement time range may be 60 s. However, other measurement time ranges are possible.

The correlating may comprise correlating the first temperature dependent signal and the second temperature dependent signal directly or using secondary information derived from the first temperature dependent signal and/or the second temperature dependent signal.

The method may comprise deriving the first temperature value from the determined first temperature dependent signal. The first temperature dependent signal may directly relate to the first temperature value or the first temperature value may be derived from the first temperature dependent signal such as by using a first temperature calibration. The first temperature calibration may comprise using at least one first temperature calibration function, e.g., a linear calibration function. Additionally or alternatively, the first temperature dependent signal may be converted into an expected electrical resistance of the membrane element $R_{mem,exp}$. For example, the first temperature calibration may comprise using at least one first temperature calibration function $f_{calibration}$ for converting the first temperature dependent signal into the expected electrical resistance of the membrane element $R_{mem,exp}$, preferably a linear first temperature calibration function with $$R_{mem,exp} = f_{calibration}(T), \text{ with}$$

$$f_{calibration}(T) = c_1 T + c_2,$$

wherein c1 and c2 are slope and offset of the linear first temperature calibration function. The first temperature calibration may be stored in the on body part of the analyte sensor, such as in the microcontroller unit. However, it is also feasible that the first temperature calibration is stored remotely from the analyte sensor, such as in a remote control of the analyte sensor. The first temperature calibration function may determined and/or provided during manufacturing of the analyte sensor, such as via factory calibration. In particular, the first temperature calibration function is specific for a batch of analyte sensors. This means that one batch of analyte sensors has in particular the same first temperature calibration function for all analyte sensors of the batch. The slope and the offset of the linear first temperature calibration function which are determined during manufacturing of the analyte sensor are also called initial slope and initial offset of the linear first temperature calibration function.

The method may comprise deriving the second temperature value from the determined second temperature dependent signal. The method may comprise converting the determined second temperature dependent signal into the second temperature value. The conversion may be performed by using at least one second temperature calibration. The second temperature calibration may comprise using at least one second temperature calibration function $f_{calibration}$ for converting the second temperature dependent signal, in particular the determined electrical resistance of the membrane element $R_{mem}$, into the second temperature value $T_{second}$ with $$T_{second} = f_{calibration}(R_{mem}).$$

The second temperature calibration function may be a linear, exponential, logarithmic or polynomic function. For example, the second temperature calibration function $f_{calibration}$ may be a linear second temperature calibration function $$f_{calibration}(R_{mem}) = c_a R_{mem} + c_b,$$

wherein $c_a$ and $c_b$ are slope and offset of the linear second temperature calibration function. The second temperature calibration function may be determined and/or provided during manufacturing of the analyte sensor such as via a factory calibration. For example, the second temperature calibration function may be stored in the on body part of the analyte sensor, in particular in the microcontroller unit. In particular, the second temperature calibration function is specific for a batch of analyte sensors. This means that one batch of analyte sensors has in particular the same second temperature calibration function for all analyte sensors of the batch. The slope and offset of the linear second temperature calibration function which are determined during manufacturing of the analyte sensor are also called the initial slope and the initial offset of the linear second temperature calibration function.

As described above, the initial offset and the initial slope of both the linear first temperature calibration function and the linear second temperature calibration function may be stored in the microcontroller unit. In an embodiment, additionally or alternatively to the initial slope and the initial offset, an in vivo slope and an in vivo offset may be determined during run-in phase of the analyte sensor by determining a relationship between measured $R_{mem}$ and the factory values of $R_{mem}$, such as by subtracting the measured $R_{mem}$ and factory values of $R_{mem}$. Determining an in vivo slope and an in vivo offset is also called an in vivo temperature calibration step. The in vivo slope and the in vivo offset describe the slope and the offset during in vivo measurements contrary to the initial slope and the initial offset which refer to the factory derived slope and offset.

The determining of the reliability of the analyte sensor may comprise comparing the correlation of the first temperature dependent signal and the second temperature dependent signal according to step c) to at least one predetermined correlation of the first temperature dependent signal and the second temperature dependent signal, determining a deviation of the correlation from the predetermined correlation and comparing the deviation to at least one threshold value. The method may comprise determining an absolute value of the deviation and comparing the absolute value to a threshold value. Alternatively, in case of non-absolute values upper and lower threshold values may be used. The analyte sensor may be considered as reliable in case the deviation is below or equal to the threshold value and otherwise, i.e., in case the deviation is above the threshold value, the analyte sensor is considered as failed.

For example, a pair of measurement values, i.e., relating to the first temperature dependent signal and the second temperature dependent signal, may be compared to a value of the stored calibration curve and in case the deviation exceeds a threshold the analyte sensor may be considered as failed. For example, the first temperature value $T_{first}$ may be measured, e.g., to be 37° C., and the measured membrane resistance $R_{mem}$ determined from the second temperature dependent signal may be determined to be 1800Ω. For the first temperature value $T_{first}$=37° C. the first temperature calibration curve may return the value of $R_{mem,exp}$=2000Ω. The threshold value may be 250Ω. In this case the analyte sensor may be considered as reliable. For example, the temperature dependency of the membrane resistance may be determined during run-in phase in vivo of the analyte sensor by performing a plurality of measurements of the first and the second temperature dependent signal. The temperature dependency in the run-in phase may be compared to a factory predetermined calibration. For example, the factory predetermined correlation may be dR/R=−7%/K with a threshold value of 2%/K and the temperature dependency in the run-in phase may be dR/R=−4%/K and the analyte sensor may be considered as failed.

The predetermined correlation may be determined in vivo and/or during manufacturing of the analyte sensor, such as in vitro. For example, the predetermined correlation may be determined during a process for manufacturing a batch of analyte sensors and may be stored as parameter in the sensor electronic. If the predetermined correlation is determined during a process of manufacturing, it is also called an initial correlation. Thus, in an embodiment of this disclosure, the terms "predetermined correlation" and "initial correlation" are used synonymously. The term "batch of analyte sensors" as used herein is a broad term and is to be given its ordinary and customary meaning to a person of ordinary skill in the art and is not to be limited to a special or customized meaning. The term specifically may refer, without limitation, to analyte sensors being manufactured from identical starting material and/or being produced on the same day.

The threshold value may be a single value and/or a range. The threshold value may be an overall threshold value for different analyte concentrations. The analyte concentration may be an analyte concentration determined simultaneously to the first and second temperature dependent signals or may be calculated within the first fault tolerance time of the sensor. In the method a plurality of threshold values may be used. For example, the threshold value may be different for different analyte concentrations. The threshold value or threshold values may be set depending on safety relevance. The term "safety relevance" as used herein is a broad term and is to be given its ordinary and customary meaning to a person of ordinary skill in the art and is not to be limited to a special or customized meaning. The term specifically may refer, without limitation, to health risk for a user. The safety relevance may be categorized into no effect on clinical outcome, little or no effect on clinical outcome, likely to affect clinical outcome, could have significant medical risk, could have dangerous consequences. The threshold value for the deviation of the correlation of the first temperature dependent signal and the second temperature dependent signal from at least one predetermined correlation may be at least one percentage error. In case the correlation of the first temperature dependent signal and the second temperature dependent signal is converted into a temperature, the threshold value for the deviation of the correlation of the first temperature dependent signal and the second temperature dependent signal from at least one predetermined correlation may be at least one maximum temperature error.

The threshold value may be independent or dependent from an analyte concentration.

For example, the threshold value for the deviation of the correlation of the first temperature dependent signal and the second temperature dependent signal from at least one predetermined correlation may be independent from an analyte concentration such as a fixed value for different ranges of analyte concentration. For example, the threshold value for the deviation of the correlation of the first temperature dependent signal and the second temperature dependent signal from at least one predetermined correlation may be in the range from −60% to 250%, preferably −50% to 50% For example, in case the correlation of the first temperature dependent signal and the second temperature dependent signal is converted into a temperature, the threshold value for the deviation of the correlation of the first temperature dependent signal and the second temperature dependent signal from at least one predetermined correlation may be from 1 K to 20 K, preferably 3 K to 7 K.

For example, the threshold values may be set depending on safety relevance such as to temperature deviations $|\Delta T|$ (i.e., absolute value of ΔT) of ≤3 K indicating not safety relevant, 3 K<$|\Delta T|$<7 K indicating likely to be safety relevant and $|\Delta T|$≥7 K indicating safety relevant. For example, a batch of the analyte sensors may have a temperature sensitivity of the measurement of the analyte concentration of −7%/K. In case of $|\Delta T|$=3 K this gives a 21% erroneous signal which is not safety relevant. In case of $|\Delta T|$=7 K this gives a −50%+50% erroneous signal which may be safety relevant, depending on the measured glucose level.

The threshold value may be dependent on a determined analyte concentration, in particular on a determined glucose concentration. The glucose concentration may be determined simultaneously to the first and second temperature dependent signals or may be determined after characterizing the analyte sensor as reliable. For example, the threshold value or the plurality of threshold values may be set according to a medical relevant error grid. The medical relevant error grid may define different zones of allowable deviations of the correlations depending on the analyte concentration depending on a risk for the user. The medical relevant error grid may define zones up to which a medical risk is acceptable. Along a straight line of these zones, the permissible percentage error that a deviation is allowed to have may change. The percentage error may be determined considering different sources such as temperature dependency of the analyte sensor. The percentage error may depend on the concentration of the analyte and may be used in reverse for the calculation of the threshold. For example, the zones may be classified with increasing risk as no effect on clinical outcome, little or no effect on clinical outcome, likely to affect clinical outcome, could have significant medical risk, could have dangerous consequences.

The threshold may be set considering the determined analyte concentration and time development of the first temperature dependent signal and the second temperature dependent signal. Specifically, a decision whether the analyte sensor is reliable or failed may be postponed to a later time point such that time development of the first temperature dependent signal and the second temperature dependent signal can be considered. The decision may be determined taking into account time development of the analyte concentration. Additionally or alternatively, the threshold may be adapted considering the analyte concentration, e.g., a trend of the analyte concentration. The term "trend of the analyte concentration" within the context of this disclosure refers to an actual tendency of the analyte concentration, such as tendency toward higher analyte concentrations or tendency toward lower analyte concentrations. The term "time development of the analyte concentration" within the context of this disclosure refers to a progression of the analyte concentration over a time span.

The reliability may be determined in step c) further considering a first fault tolerance time. The term "first fault tolerance time" as used herein is a broad term and is to be given its ordinary and customary meaning to a person of ordinary skill in the art and is not to be limited to a special or customized meaning. The term specifically may refer, without limitation, to a time range during which it has to be determined whether the analyte sensor delivers reliable measurement values, in particular, reliable analyte concentrations, without putting the user at risk. In particular, the threshold value may depend on the time and the determined analyte concentration. Taking the first fault tolerance time into account for the assessment of the reliability/patient risk, the measurement values of the analyte concentration measured during the first fault tolerance time may not be shown to the user or may be flagged as "not valid" when the analyte sensor is considered not reliable.

For example, the threshold may be set considering the determined analyte concentration, the medical relevant error grid and time development of the first temperature dependent signal and second temperature dependent signal and/or time development of the analyte concentration.

The threshold value may be stored as batch dependent parameter in the sensor electronics such as in a software or firmware of the analyte sensor. For example, a batch number of the analyte sensor may be stored in the sensor electronics. The sensor electronics may be configured for downloading corresponding parameters such as the first and/or the second temperature calibration function, from a remote control. The term "firmware" within the context of the present refers to software which is comprised in the analyte sensor, in particular in the on body part of the analyte sensor and which is stored in a non-volatile memory thereof. The term "software" within the context of this disclosure refers to software which is stored on a computer, such as a laptop and/or a smartphone and is loaded into a volatile memory during use.

As described above, the method may comprise at least one in vivo temperature calibration step. The in vivo temperature calibration step is generally performed in vivo. During manufacturing of the analyte sensor rough parameters such as range of the membrane resistance, or temperature dependency dR/R/K and/or initial slope and/or initial offset may be determined. The in vivo temperature calibration step may comprise measuring the at least one second temperature dependent signal at a time t1 and comparing the measured second temperature dependent signal with a predetermined correlation curve (i.e., initial calibration curve). The predetermined correlation curve may be determined during manufacturing, such as during manufacturing of the batch of analyte sensors and/or of a single analyte sensor and may be stored in the sensor electronics of the analyte sensor. During the in vivo temperature calibration step, the initial slope and/or the initial offset of the linear first and second temperature calibration function may be adapted to the in vivo slope and/or in vivo offset of the linear first and second temperature calibration function. This may in particular be carried out if the sensor is determined reliable in step c) and if deviations between the initial slope and/or initial offset and the in vivo slope and/or in vivo offset are found, in particular when comparing the measured second temperature dependent signal to the predetermined correlation curve. If the difference between the initial offset and the in vivo offset and/or the difference between the initial slope and the in vivo slope exceeds a threshold, the sensor may be considered not reliable, in particular, it may be considered failed.

The in vivo temperature calibration step may comprise measuring the at least one first temperature dependent signal at the time t1. The in vivo temperature calibration step may further comprise determining a theoretical or expected temperature from the measured second temperature dependent signal and comparing the theoretical or expected temperature with the first temperature value derived from the measured first temperature dependent signal. A result of the comparison may be used as in vivo value for the correlation of the first and second temperature dependent signals for step c). For example, the membrane resistance may decrease such as by 7% per K. An absolute value may fluctuate due to production tolerances such as in a range of 1 K to 30 K. If at t1 the in vivo value of the membrane resistance is, e.g., 1000 Ohms, then, in step c) said in vivo value is considered when comparing to the predetermined correlation. Additionally or alternatively, the in vivo temperature calibration step comprises measuring the at least one second temperature dependent signal at a time t1 and comparing the measured second temperature dependent signal with a predetermined correlation curve. This may be performed by comparing first and second temperature values.

The in vivo temperature calibration step may comprise determining plausibility of a calibration by performing method steps a) to c), comparing the correlation of step c) to at least one predetermined correlation, determining a deviation of the correlation from the predetermined correlation and comparing the deviation to at least one threshold value. The calibration of which the plausibility is determined may be a temperature calibration. However, within the context of this disclosure, it is also feasible that the calibration is an analyte concentration calibration which is known to the skilled person, as such and comprises, for example, a finger pricking step.

The determining of the plausibility may be performed during a run-in phase, e.g., by performing a plurality of measurements of the first and the second temperature dependent signal and determining temperature dependency of the membrane resistance during the run-in-phase. The temperature dependency in the run-in phase may be compared to a factory predetermined calibration (i.e., initial calibration). The term "run-in phase" within the context of this disclosure is a time range which begins with the insertion of the analyte sensor into a bodily tissue and ends at a point in time at which the sensor is considered sufficiently stable to report analyte valued. Typically, the run-in phase is in the range of about 0 minutes (min) to 8 hours (h), preferably in the range of 15 min to 4 hours. The calibration is considered as plausible when the deviation is below or equal to the threshold value and otherwise, i.e., in case the deviation is above the threshold value, rejected. The predetermined correlation may be determined during the initial temperature calibration step. Due to high impact of single calibration events, only those calibration events may be considered in which a deviation of the correlation from the predetermined correlation fulfills even tighter threshold values as used in step c).

As outlined above, the analyte sensor may be an in vivo sensor, specifically an in vivo continuous glucose sensor. The method may be an in-process control. The method may be performed during in-vivo measurement. The method may be performed in-operando, in particular in vivo such as during run-in phase, as defined above. Specifically, the method may be performed before or during determining of the concentration of the analyte. Additionally or alternatively, the method may be performed during manufacturing of the analyte sensor. For example, the manufacturing process may comprise the at least one temperature calibration step. The method may be used for providing a factory calibrated analyte sensor.

Furthermore, the method may be performed after the run-in phase. In this embodiment, the predetermined correlation to which the correlation of step c) is compared, is preferably the in vivo correlation which is performed during the run in time. It is to be understood that the above described embodiments and methods apply mutatis mutandis to this embodiment, as well.

The method may comprise at least one failsafe step. As used herein, the term "failsafe step" refers to at least one step ensuring to prevent generating and/or determining and/or displaying unreliable or even false measurement values. The failsafe step may be triggered depending on the determined reliability. For example, in case the determined reliability indicates "failed," the determining of the concentration of the analyte may be stopped and/or determined concentration values may be rejected and/or the analyte sensor may be rejected for use or further use. Based on the reliability, at least one failsafe decision may be determined and/or at least one failsafe action may be performed. For example, the failsafe step may comprise issuing and/or displaying an error message. The failsafe step may comprise displaying a warning message. For example, the failsafe step may comprise preventing issuing and/or displaying the analyte concentration. For example, the failsafe step may comprise a request to remove the analyte sensor. The failsafe step may be performed repeatedly, for example, in a predefined interval, such as every minute or every 5 minutes. However, other embodiments and time intervals are possible.

For example, if at a specific temperature such as at 37° C., the membrane resistance derived from the second temperature dependent signal and the expected membrane resistance at this first temperature deviate by more than a threshold value, e.g., in percentage, the analyte sensor may be considered as failed.

For example, if the first temperature value and the second temperature value deviate by more than a threshold value, e.g., in percentage, the analyte sensor may be considered as failed.

In a further aspect, a method for determining a concentration of at least one analyte in bodily fluid using at least one analyte sensor is disclosed. The method comprises determining the reliability of the analyte sensor by using a method for determining a reliability of an analyte sensor according to this disclosure. The method further comprises at least one analyte measurement step, wherein in the analyte measurement step the concentration of the analyte is determined. The determining of the concentration and the reliability may be performed independently from each other. For example, the concentration may be determined separately and in case it is determined that the reliability of the analyte sensor is not fulfilled a flag may be set that the determined concentration is not reliable.

For definitions of the features and for optional details, reference may be made to one or more of the embodiments of the method for determining a reliability as disclosed above or as disclosed in further detail below.

The term "determining a concentration of at least one analyte" generally refers to a quantitative detection of the at least one analyte. As a result of the determination, at least one signal, such as at least one measurement signal, and/or at least one measurement value may be produced and/or provided which characterizes an outcome of the determination. The signal specifically may be or may comprise at least one electronic signal such as at least one voltage and/or at least one current. The at least one signal may be or may comprise at least one analogue signal and/or may be or may comprise at least one digital signal.

As outlined above, the method for determining an analyte concentration comprises at least one analyte measurement step. For example, in case of a two-electrode-sensor, in the analyte measurement step, a potential difference may be applied across the two measurement electrodes which are in contact with a test chemical and the bodily fluid. For example, in case of a three-electrode-sensor, in the analyte measurement step the measurement voltage signal may be applied to the working electrode such that a constant potential may be applied between the working electrode and the reference electrode such that a current produced at the working electrode flows towards the counter electrode. The current may be measured at the counter electrode using I/U converter and an analog to digital converter (ADC) channel. The method furthermore may comprise at least one evaluation step, wherein current is evaluated. The at least one sensor electronics may be used for evaluating the measured current and for determining the concentration of the analyte therefrom.

As used herein, the term "sensor electronics" generally refers to at least one arbitrary device being configured for performing the named operations. For example, the sensor electronics may be configured for deriving the at least one item of information regarding the presence and/or concentration of the analyte in the bodily fluid from the current. For example, the sensor electronics may be configured for correlating the first temperature dependent signal and the second temperature dependent signal. As an example, the sensor electronics may be or may comprise one or more integrated circuits, such as one or more application-specific integrated circuits (ASICs), and/or one or more data processing devices, such as one or more computers, preferably one or more microcomputers and/or microcontrollers. Additional components may be comprised, such as one or more preprocessing devices and/or data acquisition devices, such as one or more devices for receiving and/or preprocessing of the electrode signals, such as one or more converters and/or one or more filters, measurement resistors, amplifiers and capacitors. Further, the sensor electronics may comprise one or more data storage devices. Further, the sensor electronics may comprise one or more interfaces, such as one or more wireless interfaces and/or one or more wire-bound interfaces. The sensor electronics may comprise a microprocessor, a cellular phone, a smart phone, a personal digital assistant, a personal computer, or a computer server. In particular, the sensor electronics may be located in the on body part of the analyte sensor.

This disclosure further discloses and proposes a computer program including computer-executable instructions for performing the methods according to this disclosure in one or more of the embodiments disclosed herein, when the program is executed on a processor such as on a microcontroller of the analyte sensor. Specifically, the computer program may be stored on a computer-readable data carrier. The computer program may be executed on an embedded processor and/or an external device outside the analyte sensor. Thus, specifically, one, more than one or even all of method steps, as indicated above, may be performed by using a computer or a computer network, preferably by using a computer program.

This disclosure further discloses and proposes a computer program product having program code means, in order to perform the methods according to this disclosure in one or more of the embodiments enclosed herein, when the program is executed on a processor such as on a microcontroller of the analyte sensor. Specifically, the program code means may be stored on a computer-readable data carrier.

Further, this disclosure discloses and proposes a data carrier having a data structure stored thereon, which, after loading into a processor, such as into a working memory or main memory, may execute the methods according to one or more of the embodiments disclosed herein.

This disclosure further proposes and discloses a computer program product with program code means stored on a machine-readable carrier, in order to perform the methods according to one or more of the embodiments disclosed herein, when the program is executed on a processor such as on a microcontroller of the analyte sensor. As used herein, a computer program product refers to the program as a tradable product. The product may generally exist in an arbitrary format, such as in a paper format, or on a computer-readable data carrier. Specifically, the computer program product may be distributed over a data network.

Finally, this disclosure proposes and discloses a modulated data signal which contains instructions readable by a computer system or computer network, for performing the methods according to one or more of the embodiments disclosed herein.

Preferably, referring to the computer-implemented aspects of this disclosure, one or more of the method steps or even all of the method steps of at least one of the methods according to one or more of the embodiments disclosed herein may be performed by using a computer or computer network. Thus, generally, any of the method steps including provision and/or manipulation of data may be performed by using a computer or computer network. Generally, these method steps may include any of the method steps, typically except for method steps requiring manual work, such as providing the samples and/or certain aspects of performing the actual measurements.

In a further aspect of this disclosure, an analyte sensor for determining a concentration of at least one analyte in bodily fluid is disclosed. The analyte sensor is an in vivo sensor. The analyte sensor is configured for measuring at least one first temperature dependent signal and for measuring at least one second temperature dependent signal which is different from the first temperature dependent signal and which is related to a current flow in the analyte sensor. The analyte sensor comprises at least one sensor electronics configured for correlating the first temperature dependent signal and the second temperature dependent signal for determining a reliability of the analyte sensor.

The analyte sensor may be configured for performing the methods according to this disclosure. For definitions of the features of the analyte sensor and for optional details of the analyte sensor, reference may be made to one or more of the embodiments of the methods as disclosed above or as disclosed in further detail below.

The analyte sensor may comprise at least one temperature sensor configured for measuring the first temperature dependent signal. The first temperature dependent signal may be a temperature value which is measured by the temperature sensor and/or which is determined from a signal measured by the temperature sensor.

The analyte sensor may comprises at least two measurement electrodes. The analyte sensor may be a two-electrode-sensor having two measurement electrodes or a three-electrode-sensor having three measurement electrodes or a multi-electrode-sensor having more than three measurement electrodes. Two of the measurement electrodes may be arranged on opposing sides of the analyte sensor.

The analyte sensor may comprise at least one signal generator device configured for generating at least one fast-transient voltage signal and for applying the fast-transient voltage signal to the two measurement electrodes. The sensor electronics may be configured for measuring the second temperature dependent signal in response to the applied fast-transient voltage signal.

Summarizing and without excluding further possible embodiments, the following embodiments may be envisaged:

Embodiment 1: A method for determining a reliability of an analyte sensor, wherein the analyte sensor is an in vivo sensor, the method comprising the steps:

a) measuring at least one first temperature dependent signal;
b) measuring at least one second temperature dependent signal which is different from the first temperature dependent signal and which is related to a current flow in the analyte sensor;
c) correlating the first temperature dependent signal and the second temperature dependent signal for determining the reliability of the analyte sensor.

Embodiment 2: The method according to embodiment 1, wherein the method comprises mutually monitoring of the first temperature dependent signal and of the second temperature dependent signal by using the correlation of step c) such that the analyte sensor is single fault safe.

Embodiment 3: The method according to any one of embodiments 1 or 2, wherein the analyte sensor comprises at least two measurement electrodes, wherein measuring the second temperature dependent signal in step b) comprises applying at least one fast-transient voltage signal to the measurement electrodes and measuring the second temperature dependent signal in response to the applied fast-transient voltage signal.

Embodiment 4: The method according to any one of embodiments 1 to 3, wherein the analyte sensor comprises at least one membrane element, wherein the second temperature dependent signal is or is related to an electrical resistance of the membrane element.

Embodiment 5: The method according to any one of embodiments 3 or 4, wherein the fast-transient voltage signal has a square wave signal form or a sine wave signal form.

Embodiment 6: The method according to any one of embodiments 3 to 5, wherein the fast-transient voltage signal comprises a non-continuous signal such as a pulse, wherein a pulse duration is ≤20 μs, preferably ≤10 μs.

Embodiment 7: The method according to any one of embodiments 1 to 6, wherein the first temperature dependent signal is measured by using at least one temperature sensor, wherein the first temperature dependent signal is a temperature value which is measured by the temperature sensor and/or which is determined from a signal measured by the temperature sensor.

Embodiment 8: The method according to any one of embodiments 1 to 7, wherein the first temperature dependent signal is measured in an on body part of the analyte sensor.

Embodiment 9: The method according to any one of embodiments 1 to 8, wherein the first temperature dependent signal is measured by at least one temperature sensor comprised by the on body part of the analyte sensor.

Embodiment 10: The method according to any one of embodiments 1 to 9, wherein the first temperature dependent signal and the second temperature dependent signal are independent from at least one measurement signal of an analyte concentration determined by the analyte sensor.

Embodiment 11: The method according to any one of embodiments 1 to 10, wherein the determining of the reliability of the analyte sensor comprises comparing the correlation of the first temperature dependent signal and the second temperature dependent signal according to step c) to at least one predetermined correlation of the first temperature dependent signal and the second temperature dependent signal, determining a deviation of the correlation from the predetermined correlation and comparing the deviation to at least one threshold value, wherein the analyte sensor is considered as reliable in case the deviation is below or equal to the threshold value and otherwise the analyte sensor is considered as failed.

Embodiment 12: The method according to embodiment 11, wherein the threshold value for the deviation of the correlation of the first temperature dependent signal and the second temperature dependent signal to the at least one predetermined correlation is at least one percentage error.

Embodiment 13: The method according to embodiments 11 or 12, wherein the threshold value is dependent on a determined analyte concentration.

Embodiment 14: The method according to any one of embodiments 11 to 13, wherein the predetermined correlation is determined in vivo and/or during manufacturing of the analyte sensor.

Embodiment 15: The method according to any one of embodiments 1 to 14, wherein the reliability is determined in step c) further considering a first fault tolerance time.

Embodiment 16: The method according to any one of embodiments 11 to 15, wherein the method comprises at least one failsafe step, wherein the failsafe step is triggered depending on the determined reliability.

Embodiment 17: The method according to any one of embodiments 1 to 16, wherein the method comprises at least one in vivo temperature calibration step, wherein the in vivo temperature calibration step comprises measuring the first temperature dependent signal and the second temperature dependent signal, comparing the second temperature dependent signal with a predetermined correlation curve, determining a theoretical temperature from the measured second temperature dependent signal and comparing the theoretical temperature with the measured first temperature dependent signal.

Embodiment 18: The method according to embodiment 17, wherein the temperature calibration step is performed in vivo and/or during manufacturing of the analyte sensor.

Embodiment 19: The method according to any one of embodiments 17 or 18, wherein the temperature calibration step comprises determining plausibility of a calibration by performing method steps a) to c), comparing the correlation of step c) to at least one predetermined correlation, determining a deviation of the correlation from the predetermined correlation and comparing the deviation to at least one threshold value, wherein the calibration is considered as plausible in case the deviation is below or equal to the threshold value and otherwise rejected.

Embodiment 20: The method according to any one of embodiments 1 to 19, wherein the method is performed during in vivo measurement.

Embodiment 21: A method for determining a concentration of at least one analyte in bodily fluid using at least one analyte sensor, wherein the method comprises determining a reliability of the analyte sensor by using a method for determining a reliability of an analyte sensor according to any one of embodiments 1 to 20, wherein the method further comprises at least one analyte measurement step, wherein in the analyte measurement step the concentration of the analyte is determined.

Embodiment 22: A computer program comprising program means for performing the method according to any one of embodiments 1 to 20 and/or the method according to embodiment 21 while the computer program is being executed on a processor such as on a microcontroller.

Embodiment 23: An analyte sensor for determining a concentration of at least one analyte in bodily fluid, wherein the analyte sensor is an in vivo sensor, wherein the analyte sensor is configured for measuring at least one first temperature dependent signal and for measuring at least one second temperature dependent signal which is different from the first temperature dependent signal and which is related to a current flow in the analyte sensor, wherein the analyte sensor comprises at least one sensor electronics configured for correlating the first temperature dependent signal and the second temperature dependent signal for determining a reliability of the analyte sensor.

Embodiment 24: The analyte sensor according to embodiment 23, wherein the analyte sensor comprises at least one temperature sensor configured for measuring the first temperature dependent signal, wherein the first temperature dependent signal is a temperature value which is measured by the temperature sensor and/or which is determined from a signal measured by the temperature sensor.

Embodiment 25: The analyte sensor according to any one of embodiments 23 or 24, wherein the analyte sensor comprises at least two measurement electrodes, wherein the analyte sensor comprises at least one signal generator device configured for generating at least one fast-transient voltage signal and for applying the fast-transient voltage signal to the two measurement electrodes, wherein the sensor electronics is configured for measuring the second temperature dependent signal in response to the applied fast-transient voltage signal.

Embodiment 26: The analyte sensor according to any one of embodiments 23 to 25, wherein the analyte sensor is a two-electrode-sensor having two measurement electrodes or a three-electrode-sensor having three measurement electrodes or a multi-electrode-sensor having more than three measurement electrodes.

Embodiment 27: The analyte sensor according to embodiment 26, wherein two of the measurement electrodes are arranged on opposing sides of the analyte sensor.

Embodiment 28: The analyte sensor according to any one of embodiments 23 to 27, wherein the analyte sensor is configured for performing the method according to any one of embodiments 1 to 20 and/or the method according to embodiment 21.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein.

DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

Figure 1:
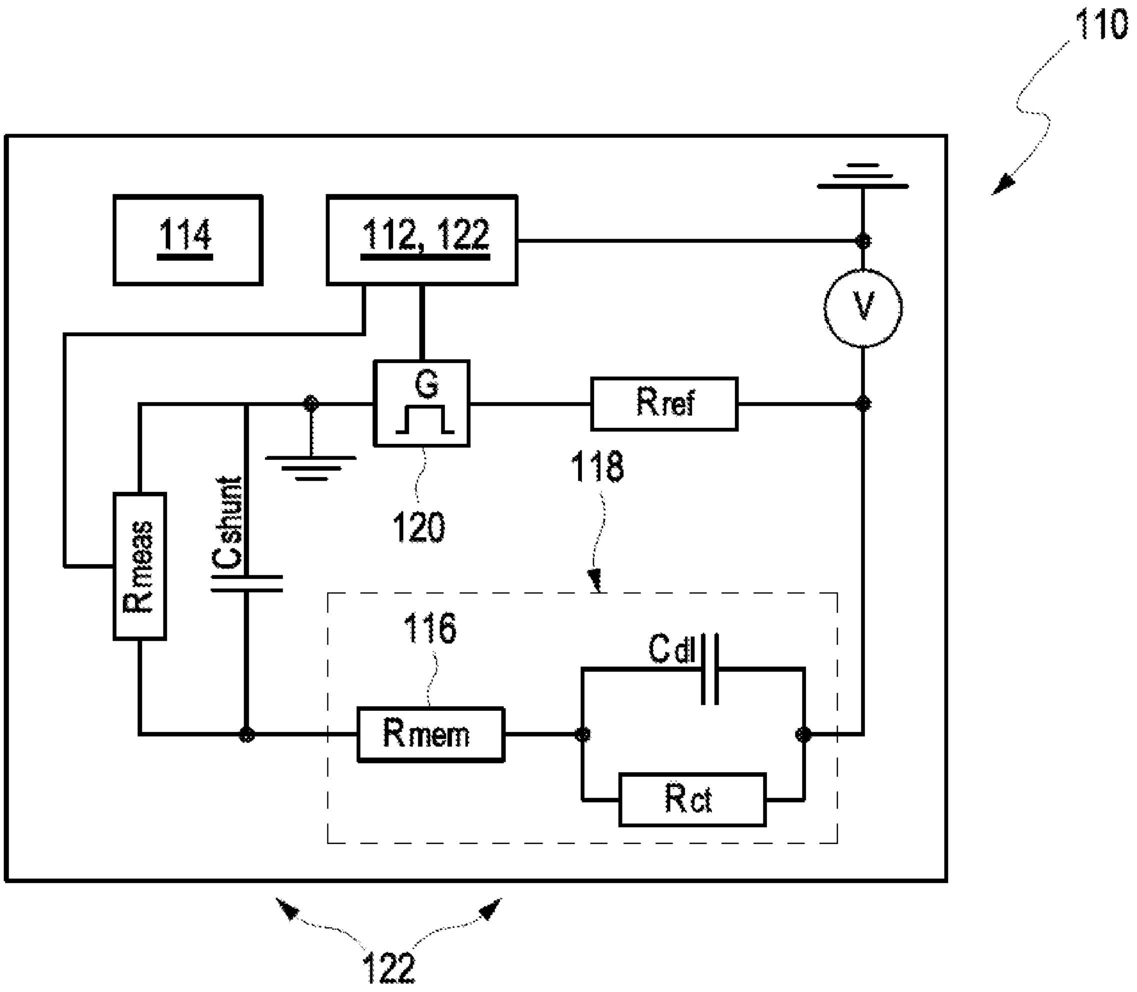
FIG. 1 shows an exemplary embodiment of an analyte sensor according to this disclosure.

FIG. 1 shows an exemplary embodiment of an analyte sensor 110 for determining a concentration of at least one analyte in bodily fluid.

The analyte sensor 110 is an in vivo sensor. The analyte sensor 110 may be configured for being at least partially implanted into a bodily tissue of a user. The analyte sensor 110 may be a subcutaneous analyte sensor. The analyte sensor 110 may be configured for implantation into a bodily tissue of the user. More specifically the analyte sensor 110 may be configured for continuous monitoring of the analyte. The analyte sensor 110 may be fully implantable or partially implantable.

The analyte sensor 110 is configured for measuring at least one first temperature dependent signal and for measuring at least one second temperature dependent signal which is different from the first temperature dependent signal and which is related to a current flow in the analyte sensor 110. The analyte sensor 110 comprises at least one sensor electronics 112 configured for correlating the first temperature dependent signal and the second temperature dependent signal for determining a reliability of the analyte sensor 110.

The first temperature dependent signal may be a signal relating directly to the first temperature or a signal from which the first temperature is derivable. The first temperature dependent signal may be or may comprise at least one electrical signal, such as at least one analogue electrical signal and/or at least one digital electrical signal. More specifically, the first temperature dependent signal may be or may comprise at least one voltage signal and/or at least one current signal. Either a raw signal may be used or a processed or a preprocess signal, such as preprocessed by filtering or the like.

The first temperature dependent signal may be measured by using at least one temperature sensor 114. The first temperature dependent signal may be measured by using a plurality of temperature sensors such as two, three or more temperature sensors 114. The first temperature dependent signal may be a temperature value which is measured by the temperature sensor 114 and/or which is determined from a signal measured by the temperature sensor 114. The temperature sensor 114 may be at least one sensor selected from the group consisting of: at least one thermistor such as at least one NTC-thermistor, PTC-thermistor, at least one thermocouple, and the like. The first temperature dependent signal may be measured in an on body part of the analyte sensor 110. The first temperature dependent signal may be measured by at least one temperature sensor 114 comprised by the on body part of the analyte sensor 110. For example, the temperature sensor 114 may be arranged in the sensor electronics 112 such as on a circuit board of the analyte sensor 110. For example, additionally or alternatively, the temperature sensor 114 may be arranged in or may be connected to a housing of the analyte sensor 110 close to the skin.

The second temperature dependent signal may be an arbitrary signal related to a current flow in the analyte sensor 110 being a measure for a second temperature and/or a second temperature gradient, in particular to a measurable temperature behavior of ion mobility within a membrane element 116, denoted in FIG. 1 with the electrical resistance Rmem of the membrane element.

The first temperature dependent signal and the second temperature dependent signal may be independent signals, in particular determined using different measurement techniques and/or sensors. For example, the first temperature dependent signal may be measured using at least one temperature sensor, whereas the second temperature dependent signal may be measured using the so called "fast-transient-technique" which is described in the following. The "fast-transient-technique" is further described, e.g., in European Patent Application No. 20 162 098.6, filed on Mar. 10, 2020, the full content of which is hereby incorporated herein by reference.

The analyte sensor 110 may comprise at least two measurement electrodes 118. The at least two measurement electrodes 118 may be designed such that an electrochemical reaction may take place at one or more of the measurement electrodes. The measurement electrodes 118 may be embodied such that an oxidation reaction and/or reduction reaction may take place at one or more of the measurement electrodes.

One of the measurement electrodes 118 may be designed as working electrode. The working electrode may comprise at least one test chemical. The working electrode may fully or partially be covered with at least one test chemical, specifically at least one test chemical comprising at least one enzyme for detecting the at least one analyte. As an example, glucose oxidase (GOx) or glucose dehydrogenase (GDH) may be used. The test chemical, further, may comprise additional materials, such as binder materials, electrode particles, mediators or the like. Thus, as an example, the test chemical may comprise at least one enzyme, carbon particles, a polymer binder and $MnO_2$ particles. In another preferred embodiment, the test chemical may comprise a mediator polymer comprising a polymeric material and a metal containing complex, for example, a modified poly (vinylpyridine) backbone loaded with poly(bi-imidizyl) Os complexes covalently coupled through a bidentate linkage. Further, the at least one test chemical may be comprised in a single layer, or the test chemical may comprise a plurality of layers, such as one layer having the at least one enzyme and one or more additional layers having one or more additional functions, such as one or more diffusion barriers and/or one or more biocompatibility layers.

The other one of the measurement electrodes 118 may be designed as counter or auxiliary electrode. The counter electrode may be a part of the implanted or partially implanted analyte sensor 110, or may be an individual electrode, which is either implanted or partially implanted or placed somewhere else on the body, e.g., on the skin surface. In case of the analyte sensor 110 comprises a two-electrode system as measurement electrodes 118, the counter electrode may complete the circuit such that charge can flow through an electrochemical cell, also denoted electrochemical system, given by the working electrode, the counter electrode and an electrolyte, such as the bodily fluid, and may maintain a constant counter electrode potential, also referred to as a constant reference potential, regardless of current.

Additionally, the analyte sensor 110 may comprise at least one reference electrode. The reference electrode may be configured for being a reference for measuring and/or controlling a potential of the working electrode. The reference electrode may have a stable and well-known electrode potential. The electrode potential of the reference electrode may preferably be highly stable.

One of the measurement electrodes may have several functionalities, as for instance, combined reference and counter electrode, which has both, the function of the reference and counter electrodes, which means it provides a reference potential and balances the current flow from the working electrode.

At least one of the measurement electrodes 118 comprises the at least one membrane 116. Specifically, the membrane may be applied to the working electrode. The membrane 116 may comprise at least one polymer. The membrane 116 may be applied to the working electrode as thin polymer film. For example, the membrane 116 may be or may comprise Poly-(4-(N-(3-sulfonatopropyl) pyridinium)-co-(4vinyl-pyridine)-co-styrene (5%/90%/5%) or hydrophilic Polyurethane (HP60D20), for example, available from Lubrizol®. For example, the membrane element 116 may comprise at least one of the following polymer classes and/or their copolymer: Poly(4 vinyl pyridine), Polymethacrylate, Polyacrylate, Polyvinyl pyrrolidone, Polyvinyl alcohol (PVA), Polyethylene glycol.

The membrane 116 may have at least one membrane property. Specifically, the membrane property may be permeability of the membrane 116. Permeability of the membrane 116 can be determined via determining an electrical resistance of the membrane Rmem. Permeability of the membrane 116 may be proportional to the membranes electrical resistance Rmem. Without being bound by theory, conductivity of bodily fluid is directly linked to so-called total dissolved solids whereby ions, such as H+, OH−, Na+, K+, Cl− and other have the most contribution. Therefore, also conductivity of the membrane which has taken up the bodily fluid is directly linked to said total dissolved solids. The more charge carriers are present and the more mobile they are, the lower is a measured electrical resistance of the membrane element 116, by otherwise constant conditions, such as, e.g., cell geometry. Thus, the electrical resistance $R_{mem}$, or reversely, electric conductivity of the membrane element 116 may depend on quantity and mobility of ions present in the membrane element 116.

The membrane property, in particular the permeability, may depend on temperature. The second temperature dependent signal may be or may be related to an electrical resistance $R_{mem}$ of the membrane element 116. Permeability of the membrane element 116 may depend on temperature, as it directly influences the ions mobility within the membrane element. The temperature at an insertion site of the analyte sensor 110 may not be constant. Intrinsic properties of the membrane element 116 may change during storage of the analyte sensor such as due to storage conditions. Such changes may lead to changes in permeability and may lead to non-reliable measurements.

The analyte sensor 110 may comprises at least one signal generator device 120, denoted with "G" in FIG. 1, configured for generating at least one fast-transient voltage signal and for applying the fast-transient voltage signal to the two measurement electrodes 118. The sensor electronics 112 may be configured for measuring a response signal, in particular the second temperature dependent signal, in response to the applied fast-transient voltage signal.

FIG. 1 shows a simplified circuit of the analyte sensor 110. The simplified circuit comprises a sensor, represented as a simple Randle's circuit, a reference resistor $R_{ref}$, a measurement resistor $R_{meas}$, a shunt capacitor $C_{shunt}$, the signal generator device 120. The Randle's circuit comprises the charge transfer resistance $R_{ct}$, which represents the diffusion limited analyte current, double layer capacitance $C_{dl}$ at the electrode surface and the membrane element resistance $R_{mem}$. The signal generator 120, in this embodiment a voltage source G, is configured for generating the at least one fast-transient voltage signal and applying it to a membrane comprising circuit serially connected with a reference resistor $R_{ref}$, wherein the membrane element 116 has a resistance $R_{mem}$. In particular, the signal generator device 120 may be configured for applying a measurement voltage signal, in particular a DC base voltage, and fast-transient voltage. During the base voltage is applied, the current flows through all four resistors in the circuit. There is no current flow through the capacitors, as they are charged to the corresponding level. The $R_{ct}$ may be few orders of magnitude larger than $R_{mem}$, such that the voltage drop at the $R_{mem}$ can be neglected in the first approximation. The same is valid for the $R_{ref}$, which is chosen to be roughly the same value as the $R_{mem}$. The value for $R_{meas}$ may be chosen at the way, to get substantial voltage drop at it, which is then measured, e.g., by an additional voltmeter or electrometer which is not shown in the scheme, and converted in the sensor current signal, thus the value of the $R_{meas}$ is roughly of the same order of magnitude as the $R_{ct}$. Since the voltage drop at the $R_{meas}$ is substantial, it is compensated by the voltage source, which is in the feedback with the current measuring unit based on the $R_{meas}$. The equivalent series resistance of the electrochemical system may be determined by $$R_{mem} = R_{ref}\frac{\Delta V_{prop}}{\Delta V_{ex} - \Delta V_{prop}} = R_3\frac{V_{prop,duringPulse} - V_{prop,beforePulse}}{(V_{ex,duringPulse} - V_{ex,beforePulse}) - (V_{prop,duringPulse} - V_{prop,beforePulse})}$$

wherein $V_{prop,beforePulse}$ refers to the voltage at the working electrode before applying the fast-transient voltage signal, $V_{prop,duringPulse}$ refers to the voltage at the working electrode during applying the fast-transient voltage signal, $V_{ex,beforePulse}$ refers to the voltage signal at the reference resistor $R_{ref}$ before applying the fast-transient voltage signal, $V_{ex,duringPulse}$ refers to the voltage signal at the reference resistor during applying the fast-transient voltage signal. Before the application of the fast-transient voltage signal $V_{ex,beforePulse}$ may refer to a voltage at the reference resistor $R_{ref}$ in response to the measurement voltage signal. After the application of the fast-transient voltage signal $V_{ex,duringPulse}$ may refer to the voltage at the reference resistor $R_{ref}$ in response to the measurement voltage signal and due to the propagation of the fast-transient voltage signal.

Measuring the second temperature dependent signal may comprise applying the at least one fast-transient voltage signal to the measurement electrodes 118 and measuring the second temperature dependent signal in response to the applied fast-transient voltage signal. The fast-transient voltage signal may be at least one arbitrary voltage change in between two measurement electrodes 118. The arbitrary voltage change may have fast transient signal flanks, in particular two very steep edges. The fast-transient voltage signal may comprise a square wave signal form and/or a sine wave signal form. The fast-transient voltage signal may comprise a non-continuous signal such as a pulse. Specifically, the fast-transient voltage signal may comprise a fast transition square wave. The pulse may have a transient change in the amplitude of the signal from a first value, also denoted baseline value, to a second value, followed by a return to the baseline value or at least approximately to the baseline value. The second value may be a higher or lower value than the baseline value. A pulse duration may be ≤50 μs, preferably ≤20 μs, more preferably ≤10 μs. The duration of the single pulse must be sufficiently long to be able to record its propagation. The duration of the single pulse must be preferentially short, in order to not excite the system electrochemically.

The response signal may be a measured propagation of the applied fast-transient voltage signal. The response signal may be a change of the applied fast-transient voltage signal. The response signal may directly or indirectly refer to equivalent series resistance of the analyte sensor. The response signal may be the ohmic and capacitive characterization of the analyte sensor in its in-vivo surroundings. In particular, the response signal does not relate to current response. The response voltage may be determined either at a known reference resistor or at the membrane element 116.

The measuring of the response signal, in particular of the second temperature dependent signal, may be performed using the at least one measurement unit 122. The measurement unit 122 may be configured for measuring the response signal generated in response to fast-transient voltage signal. The measurement unit 122 may further be configured for measuring the current at the counter electrode for determining a concentration of at least one analyte in bodily fluid. The measurement unit 122 may be configured for receiving the response signal and the current at the counter electrode at the same time or at at least two different time points. The measurement unit 122 may comprise at least one potentiostat such as at least one digital potentiostat or at least one analog potentiostat. Operating principles of potentiostats and galvanostats are generally known to the person skilled in the art. In the following the measurement unit will be described with reference to a potentiostat.

The first temperature dependent signal and the second temperature dependent signal may be independent from at least one measurement signal of an analyte concentration measured by the analyte sensor 110. The potentiostat may be configured for generating and/or applying of at least one measurement voltage signal, in particular a polarizing potential or voltage, for measuring the measurement signal of an analyte concentration in response. The measurement voltage signal may be a voltage signal used for determining, in particular measuring, the concentration of the analyte. The measurement voltage signal may be different to the fast-transient voltage signal. In particular, the measurement voltage signal may be longer compared to the fast-transient voltage signal. The measurement voltage signal may be a permanent signal, not a pulsed one. The measurement voltage signal may be adjusted from time to time or continuously in order to give the analyte sensor 110 its polarization voltage, preferably, in order to keep the predefined polarization voltage at the analyte sensor 110. The measurement voltage signal may be a continuous direct current (DC) signal which polarizes the electrochemical cell, and serves as the "motor" for the amperometric measurement of the analyte reducing or oxidizing GOx across the electrochemical cell. The fast-transient voltage signal may be a voltage pulse with high frequency that only characterizes the capacitive and ohmic parts of the electrochemical cell. Therefore, the measurement voltage signal and the fast-transient voltage signal may not influence each other, since they have completely different time domains.

In a two-electrode system, the measurement voltage signal and the fast-transient voltage signal may be applied to the same electrodes 118. In a three-electrode system a voltage is determined and controlled between the working electrode and the reference electrode. In order to achieve this, the potentiostat may regulate the potential of the counter electrode. The fast-transient voltage signal may be applied between the counter and the working electrode or between the working and the reference electrode or between the counter and the reference electrode.

The sensor electronics 112 may be configured for correlating of the first temperature dependent signal and the second temperature dependent signal by determining a relationship between the first temperature dependent signal and the second temperature dependent signal.

The correlating may comprise comparing a first temperature value determined from the first temperature dependent signal and a second temperature value determined from the second temperature dependent signal. The correlating may comprise determining a deviation between the first temperature value determined from the first temperature dependent signal and the second temperature value determined from the second temperature dependent signal. If the deviation $\Delta T = T_{first} - T_{second}$ between the first temperature value $T_{first}$ and the second temperature value $T_{second}$ is determined to exceed a threshold value $\Delta T_{threshold}$, the analyte sensor is considered as failed.

The correlating may comprise correlating at least one actual value of the first temperature dependent signal, in particular at least one first actual temperature value, and at least one actual value of the second temperature dependent signal, in particular at least one second actual temperature value. The respective actual value may be a mean value determined from a plurality of measurements such as during a measurement time range. For example, the measurement time range may be 60 s. However, other measurement time ranges are possible.

The correlating may comprise correlating the first temperature dependent signal and the second temperature dependent signal directly or using secondary information derived from the first temperature dependent signal and/or the second temperature dependent signal.

The method may comprise deriving the first temperature value, from the determined first temperature dependent signal. The first temperature dependent signal may directly relate to the first temperature value or the first temperature value may be derived from the first temperature dependent signal such as by using a first temperature calibration. The first temperature calibration may comprise using at least one first temperature calibration function e.g., a linear calibration function. Additionally or alternatively, the first temperature dependent signal may be converted into an expected electrical resistance of the membrane element $R_{mem,exp}$. For example, the first temperature calibration may comprise using at least one first temperature calibration function $f_{calibration}$ for converting the first temperature dependent signal into the expected electrical resistance of the membrane element $R_{mem,exp}$, preferably a linear first temperature calibration function with $$R_{mem,exp}=f_{calibration}(T), \text{ with}$$

$$f_{calibration}(T)=c_1T+c_2,$$

wherein c1 and c2 are slope and offset of the linear first temperature calibration function. The first temperature calibration may be stored in the on body part of the analyte sensor such as in the microcontroller unit. The first temperature calibration function may be determined and/or provided during manufacturing of the analyte sensor, such as via factory calibration.

The method may comprise deriving the second temperature value, from the determined second temperature dependent signal. The method may comprise converting the determined second temperature dependent signal into the second temperature value. The conversion may be performed by using at least one second temperature calibration. The second temperature calibration may comprise using at least one second temperature calibration function $f_{calibration}$ for converting the second temperature dependent signal, in particular the determined electrical resistance of the membrane element $R_{mem}$, into the second temperature value $T_{second}$ with $$T_{second}=f_{calibration}(R_{mem}).$$

The second temperature calibration function may be a linear, exponential, logarithmic or polynomic function. For example, the second temperature calibration function $f_{calibration}$ may be a linear second temperature calibration function $$f_{calibration}(R_{mem})=c_aR_{mem}+c_b,$$

wherein $c_a$ and $c_b$ are slope and offset of the linear second temperature calibration function. The second temperature calibration function may be determined and/or provided during manufacturing of the analyte sensor such as via a factory calibration. For example, the second temperature calibration function may be stored in the on body part of the analyte sensor, in particular in the microcontroller unit.

The initial offset and the initial slope of both the linear first temperature calibration function and the linear second temperature calibration function may be stored in the microcontroller unit. Additionally to the initial slope and the initial offset, an in vivo slope and an in vivo offset may be determined during run-in phase of the analyte sensor by determining a relationship between measured $R_{mem}$ and the factory values of $R_{mem}$, such as by subtracting the measured $R_{mem}$ and factory values of $R_{mem}$.

The sensor electronics 112 may be configured for determining of the reliability of the analyte sensor 110 by comparing the correlation of the first temperature dependent signal and the second temperature dependent signal to at least one predetermined correlation of the first temperature dependent signal and the second temperature dependent signal, determining a deviation of the correlation from the predetermined correlation and comparing the deviation to at least one threshold value. The method may comprise determining an absolute value of the deviation and comparing the absolute value to a threshold value. Alternatively, in case of non-absolute values upper and lower threshold values may be used. The analyte sensor 110 may be considered as reliable in case the deviation is below or equal to the threshold value and otherwise, i.e., in case the deviation is above the threshold value, the analyte sensor 110 is considered as failed.

The predetermined correlation may be determined in vivo and/or during manufacturing of the analyte sensor 110, such as in vitro. For example, the predetermined correlation may be determined during a process for manufacturing a batch of analyte sensors and may be stored as parameter in a sensor electronic.

The threshold value may be a single value and/or a range. The threshold value may be an overall threshold value for different analyte concentrations. The sensor electronics 112 may be configured for using a plurality of threshold values. For example, the threshold value may be different for different analyte concentrations. The threshold value or threshold values may be set depending on safety relevance. The threshold value for the deviation of the correlation of the first temperature dependent signal and the second temperature dependent signal from at least one predetermined correlation may be at least one percentage error. In case the correlation of the first temperature dependent signal and the second temperature dependent signal is converted into a temperature, the threshold value for the deviation of the correlation of the first temperature dependent signal and the second temperature dependent signal from at least one predetermined correlation may be at least one maximum temperature error.

The threshold value may be independent or dependent from an analyte concentration.

For example, the threshold value for the deviation of the correlation of the first temperature dependent signal and the second temperature dependent signal from at least one predetermined correlation may be independent from an analyte concentration such as a fixed value for different ranges of analyte concentration. For example, the threshold value for the deviation of the correlation of the first temperature dependent signal and the second temperature dependent signal from at least one predetermined correlation may be in the range from −60% to 250%, preferably −50% to 50%. For example, in case the correlation of the first temperature dependent signal and the second temperature dependent signal is converted into a temperature, the threshold value for the deviation of the correlation of the first temperature dependent signal and the second temperature dependent signal from at least one predetermined correlation may be from 1 K to 20 K, preferably 3 K to 7 K.

For example, the threshold values may be set depending on safety relevance such as to temperature deviations $|\Delta T|$ of ≤3K indicating not safety relevant, 3 K<$|\Delta T|$<7 K indicating likely to be safety relevant and $|\Delta T|$≤7K indicating safety relevant. For example, a batch of the analyte sensor may have a temperature sensitivity of the measurement of the analyte concentration of −7%/K. In case of $|\Delta T|$=3 K this gives a 21% erroneous signal which is not safety relevant. In case of $|\Delta T|=7$ K this gives a −50%+50% erroneous signal which may be safety relevant, depending on the measured glucose level.

The threshold value may be dependent on a determined analyte concentration, in particular on a determined glucose concentration. For example, the threshold value or the plurality of threshold values may be set according to a medical relevant error grid. The medical relevant error grid may define different zones of allowable deviations of the correlations depending on the analyte concentration depending on a risk for the user. The medical relevant error grid may define zones up to which a medical risk is acceptable. Along a straight line of these zones, the permissible percentage error that a deviation is allowed to have may change. The percentage error may be determined considering different sources such as temperature dependency of the analyte sensor. The percentage error may depend on the concentration of the analyte and may be used in reverse for the calculation of the threshold. For example, the zones may be classified with increasing risk as no effect on clinical outcome, little or no effect on clinical outcome, likely to affect clinical outcome, could have significant medical risk, could have dangerous consequences.

The threshold may be set considering the determined analyte concentration and time development of the first temperature dependent signal and the second temperature dependent signal. Specifically, a decision whether the analyte sensor 110 is reliable or failed may be postponed to a later time point such that time development of the first temperature dependent signal and the second temperature dependent signal can be considered. The decision may be determined taking into account time development of the analyte concentration. Additionally or alternatively, the threshold may be adapted considering the analyte concentration, e.g., a trend of the analyte concentration. The reliability may be determined further considering a first fault tolerance time. The first fault tolerance time may be the time range during which it has to be determined whether the analyte sensor delivers reliable measurement values, in particular reliable analyte concentrations, without putting the user at risk. In particular, the threshold value may depend on the time and the determined analyte concentration. Taking the first fault tolerance time into account for the assessment of the reliability/patient risk, the measurement values of the analyte concentration measured during the first fault tolerance time may not be shown to the user or may be flagged as "not valid" when the analyte sensor is considered not reliable.

For example, the threshold may be set considering the determined analyte concentration, the medical relevant error grid and time development of the first temperature dependent signal and second temperature dependent signal and/or time development of the analyte concentration.

The threshold value may be stored as charge dependent parameter in a software of the analyte sensor 110. For example, the threshold value and correlation coefficients may be stored such as in firmware of the analyte sensor 110.

Figure 2:
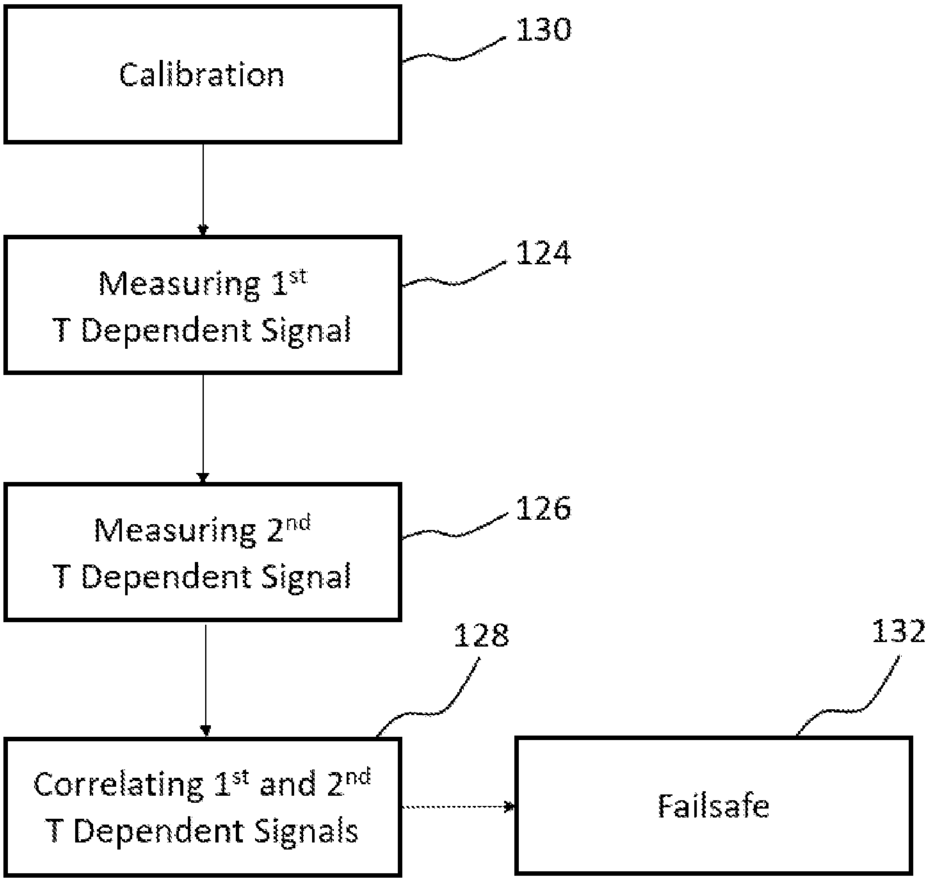
FIG. 2 is a flow chart of a method for determining the reliability of an analyte sensor according to this disclosure.

The sensor electronics 112 may be configured for performing at least one in vivo temperature calibration step 130, see FIG. 2. The in vivo temperature calibration step 130 is generally performed in vivo. During manufacturing of the analyte sensor 110 rough parameters such as range of the membrane resistance, or temperature dependency dR/R/K and/or initial slope and/or initial offset may be determined. The in vivo temperature calibration step 130 may comprise measuring the at least one second temperature dependent signal at a time t1 and comparing the measured second temperature dependent signal with a predetermined correlation curve (i.e., initial calibration curve). The predetermined correlation curve may be determined during manufacturing of the batch of the analyte sensors 110 and may be stored in the sensor electronics 112 of the analyte sensor. During the in vivo temperature calibration step 130, the initial slope and/or the initial offset of the linear first and second temperature calibration function may be adapted to the in vivo slope and/or the in vivo offset of the linear first and second temperature calibration function. This may in particular be carried out if the sensor is determined reliable in step c) and if deviations between the initial slope and/or initial offset and the in vivo slope and/or in vivo offset are found, in particular when comparing the measured second temperature dependent signal to the predetermined correlation curve.

The in vivo temperature calibration step 130 may comprise measuring the at least one first temperature dependent signal at the time t1. The in vivo temperature calibration step 130 may further comprise determining a theoretical or expected temperature from the measured second temperature dependent signal and comparing the theoretical or expected temperature with the first temperature value derived from the measured first temperature dependent signals for step c). For example, the membrane resistance may decrease such as by 7% per K. An absolute value may fluctuate due to production tolerances such as in a range of 1 K to 30 K. If at t1 the in vivo value of the membrane resistance is, e.g., 1000 Ohm, then, in step c) said in vivo value is considered when comparing to the predetermined correlation. Additionally or alternatively, the in vivo temperature calibration step comprises measuring the at least one second temperature dependent signal at a time t1 and comparing the measured second temperature dependent signal with a predetermined correlation curve. This may be performed by comparing first and second temperature values.

The sensor electronics 112 may be configured for performing at least one failsafe step 132, see FIG. 2. The failsafe step 132 may comprise ensuring to prevent generating and/or determining and/or displaying unreliable or even false measurement values. The failsafe step 132 may be triggered depending on the determined reliability. For example, in case the determined reliability indicates "failed," the determining of the concentration of the analyte may be stopped and/or determined concentration values may be rejected and/or the analyte sensor 110 may be rejected for use or further use. Based on the reliability, at least one failsafe decision may be determined and/or at least one failsafe action may be performed. For example, the failsafe step may comprise issuing and/or displaying an error message. The failsafe step 132 may comprise displaying a warning message such as a red LED signalizing an error. For example, the failsafe step 132 may comprise preventing issuing and/or displaying the analyte concentration. For example, the failsafe step may comprise a request to remove the analyte sensor. The failsafe step 132 may be performed repeatedly, for example, in a predefined interval, such as every minute or every 5 minutes. However, other embodiments and time intervals are possible.

FIG. 2 shows a flow chart of a method for determining a reliability of an analyte sensor 110 according to this disclosure.

The method comprising the steps:

a) measuring at least one first temperature dependent signal (denoted with reference number 124);

b) measuring at least one second temperature dependent signal which is different from the first temperature dependent signal and which is related to a current flow in the analyte sensor 110 (denoted with reference number 126);

c) correlating the first temperature dependent signal and the second temperature dependent signal for determining the reliability of the analyte sensor 110 (denoted with reference number 128).

The method may further comprise the at least one in vivo temperature calibration step 130. The method may further comprise the at least one failsafe step 132.

Figure 3:
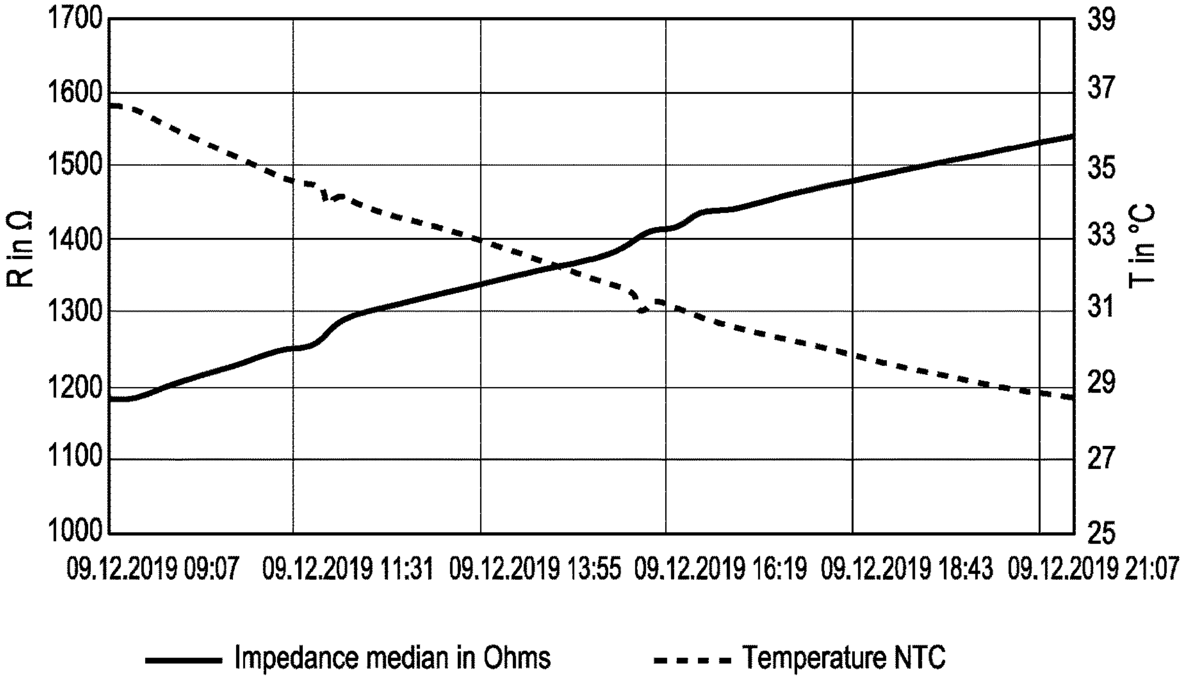
FIG. 3 shows experimental results of a measured first temperature dependent signal and a measured second temperature dependent signal.

FIG. 3 shows experimental results of a measured first temperature dependent signal and a measured second temperature dependent signal using a two-electrode analyte sensor 110. In particular, the first temperature dependent signal T in ° C. and the second temperature dependent signal R in Ω is shown as function of time. The first temperature dependent signal and the second temperature dependent signal were measured under controlled temperature changes from 25 to 39° C. over 9 hours. The first temperature dependent signal was measured using an NTC thermistor. The impedance median may refer to a median value of measurement values of membrane resistance determined within 60 s. A correlation between the first temperature dependent signal and the second temperature dependent signal can be observed.

Figure 4A:
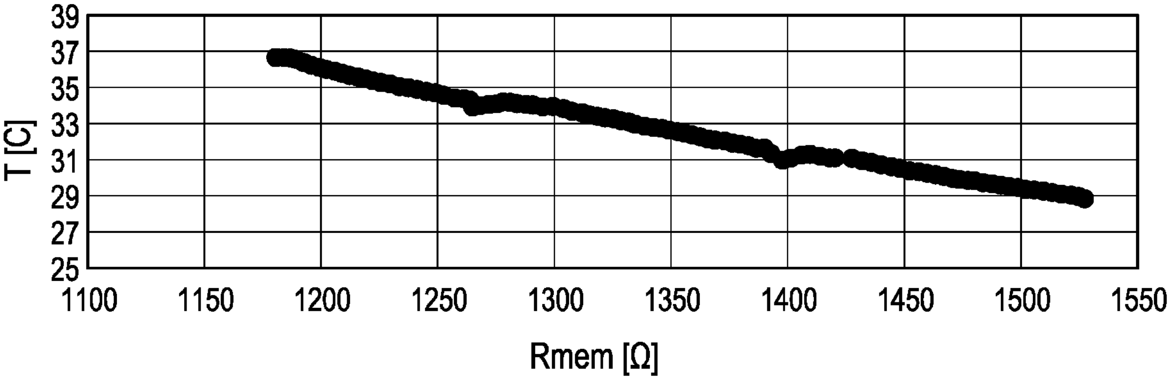
FIGS. 4A and 4B show further experimental results of temperature dependency of the membrane resistance.
Figure 4B:
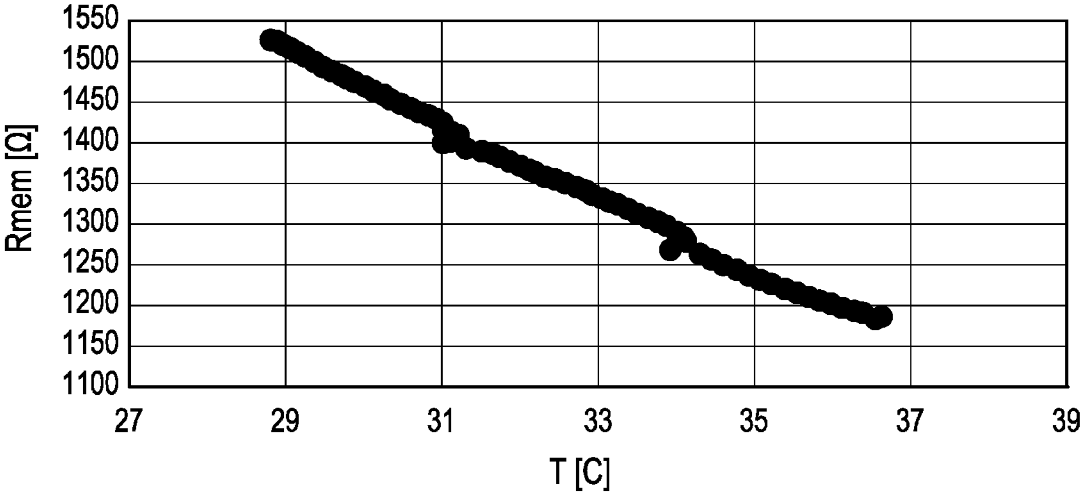

FIGS. 4A and 4B show further experimental results of temperature dependency of the membrane resistance. In FIG. 4A the membrane resistance $R_{mem}$ in Ω, as a function of the first temperature dependent signal in ° C., which was measured using an NTC thermistor, is shown. A linear fit result may be $y=-0.022x+62.28$ for this experimental result. FIG. 4B shows an exemplary predetermined correlation of the membrane resistance in Ω with the temperature in ° C. In this case, the calibration function may be $T_{second}=-45.309\ R_{mem}+2826.7$. In case a deviation between the measured membrane resistance for a given temperature and the expected impedance derived from said predetermined correlation exceeds a threshold the analyte sensor is considered as failed.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

LIST OF REFERENCE NUMBERS

110 analyte sensor
112 sensor electronics
114 temperature sensor
116 membrane element
118 measurement electrodes
120 signal generator device
122 measurement unit
124 measuring at least one first temperature dependent signal
126 measuring at least one second temperature dependent signal
128 correlating
130 in vivo temperature calibration step
132 failsafe step

What is claimed is:

1. A method for determining reliability of an in vivo analyte sensor, the method comprising:

a) measuring a first temperature dependent signal;

b) measuring a second temperature dependent signal which is different from the first temperature dependent signal and which is related to a current flow in the in vivo analyte sensor; and c) correlating the first temperature dependent signal and the second temperature dependent signal for determining the reliability of the in vivo analyte sensor.

2. The method according to claim 1, wherein the in vivo analyte sensor comprises at least two measurement electrodes, wherein measuring the second temperature dependent signal in step b) comprises applying a fast-transient voltage signal to the measurement electrodes and measuring the second temperature dependent signal in response to the applied fast-transient voltage signal.

3. The method according to claim 1, wherein the in vivo analyte sensor comprises a membrane, wherein the second temperature dependent signal is related to an electrical resistance of the membrane.

4. The method according to claim 1, wherein the first temperature dependent signal is a temperature value which is measured by a temperature sensor and/or which is determined from a signal measured by the temperature sensor.

5. The method according to claim 1, wherein the first temperature dependent signal is measured by a temperature sensor comprising an on body part of the analyte sensor.

6. The method according to claim 1, wherein the first temperature dependent signal and the second temperature dependent signal are independent from at least one measurement signal of an analyte concentration determined by the analyte sensor.

7. The method according to claim 1, wherein the determining of the reliability of the analyte sensor comprises comparing the correlation of the first temperature dependent signal and the second temperature dependent signal according to step c) to at least one predetermined correlation of the first temperature dependent signal and the second temperature dependent signal, determining a deviation of the correlation from the predetermined correlation, and comparing the determined deviation to at least one threshold value, wherein the analyte sensor is considered reliable when the deviation is below or equal to the threshold value and otherwise the analyte sensor is considered to be failed.

8. The method according to claim 7, wherein the threshold value for the deviation of the correlation of the first temperature dependent signal and the second temperature dependent signal to the at least one predetermined correlation is at least one percentage error.

9. The method according to claim 7, wherein the threshold value is dependent on a determined analyte concentration.

10. The method according to claim 7, wherein the predetermined correlation is determined in vivo and/or during manufacturing of the analyte sensor.

11. The method according to claim 7, wherein the method comprises at least one failsafe step, wherein the failsafe step is triggered when the analyte sensor is considered to be failed.

12. An in vivo analyte sensor for determining concentration of an analyte in bodily fluid, wherein the in vivo analyte sensor is configured for measuring a first temperature dependent signal and for measuring a second temperature dependent signal which is different from the first temperature dependent signal and which is related to a current flow in the analyte sensor, wherein the in vivo analyte sensor comprises at least one sensor electronics configured for correlating the first temperature dependent signal and the second temperature dependent signal for determining a reliability of the analyte sensor.

13. The in vivo analyte sensor according to claim 12, wherein the in vivo analyte sensor is a two-electrode-sensor having two measurement electrodes or a three-electrode-sensor having three measurement electrodes or a multi-electrode-sensor having more than three measurement electrodes.

14. The in vivo analyte sensor according to claim 13, wherein two of the measurement electrodes are arranged on opposing sides of the in vivo analyte sensor.

15. The in vivo analyte sensor according to claim 12, wherein the in vivo analyte sensor is configured for performing the following steps:

a) measuring a first temperature dependent signal;

b) measuring a second temperature dependent signal which is different from the first temperature dependent signal and which is related to a current flow in the in vivo analyte sensor; and c) correlating the first temperature dependent signal and the second temperature dependent signal for determining the reliability of the in vivo analyte sensor.

16. The in vivo analyte sensor according to claim 15, wherein correlating the first temperature dependent signal and the second temperature dependent signal comprises comparing a first temperature value determined from the first temperature dependent signal and a second temperature value determined from the second temperature dependent signal.

17. The in vivo analyte sensor according to claim 16 wherein:

the in vivo sensor comprises an on body part having a temperature sensor and the temperature sensor is used when measuring the first temperature dependent signal; and the in vivo analyte sensor comprises a membrane and the second temperature dependent signal is related to an electrical resistance of the membrane.

18. The method according to claim 1, wherein correlating the first temperature dependent signal and the second temperature dependent signal comprises comparing a first temperature value determined from the first temperature dependent signal and a second temperature value determined from the second temperature dependent signal.

19. The method according to claim 18, wherein the in vivo sensor comprises an on body part having a temperature sensor and the temperature sensor is used when measuring the first temperature dependent signal; and the in vivo analyte sensor comprises a membrane and the second temperature dependent signal is related to an electrical resistance of the membrane.

* * * * *